United States Patent
Sy et al.

(10) Patent No.: US 8,158,373 B2
(45) Date of Patent: Apr. 17, 2012

(54) METHOD OF DETECTING CANCER AND EVALUATING CANCER PROGNOSIS

(75) Inventors: Man-Sun Sy, Shaker Heights, OH (US); Wei Xin, Solon, OH (US)

(73) Assignee: Case Western Reserve University, Cleveland, OH (US)

( * ) Notice: Subject to any disclaimer, the term of this patent is extended or adjusted under 35 U.S.C. 154(b) by 265 days.

(21) Appl. No.: 12/410,867

(22) Filed: Mar. 25, 2009

(65) Prior Publication Data

US 2009/0246798 A1 Oct. 1, 2009

Related U.S. Application Data

(60) Provisional application No. 61/039,290, filed on Mar. 25, 2008.

(51) Int. Cl.
*G01N 33/574* (2006.01)
(52) U.S. Cl. .......................................... 435/7.23; 435/7.1
(58) Field of Classification Search .......................... None
See application file for complete search history.

(56) References Cited

U.S. PATENT DOCUMENTS

2005/0260639 A1* 11/2005 Nakamura et al. ................. 435/6
2009/0252721 A1* 10/2009 Buschmann et al. ......... 424/130.1

OTHER PUBLICATIONS

Tockman et al (Cancer Res., 1992, 52:2711s-2718s.*
Chen et al., J Cell Biochem, 2002, 84:68-83.*
Waneck et al, Nature, 1988, 242:697-699.*
Kim et al, Modern Pathology, Feb. 2007, 20 Suppl 2:102A.*
Ashok et al, Mol Biol, 2008, 19:3463-3476.*

* cited by examiner

*Primary Examiner* — Misook Yu
*Assistant Examiner* — Mark Halvorson
(74) *Attorney, Agent, or Firm* — Tarolli, Sundheim, Covell & Tummino LLP

(57) ABSTRACT

A method of detecting cancer in a subject is provided. One step of the method includes obtaining a bodily sample from the subject. Next, the level of pro-prion protein (pro-PrP) in the bodily sample is detected. The level of pro-PrP in the bodily sample is then compared to a control level. An increased level of pro-PrP in the bodily sample as compared to the control level indicates that the subject has cancer or an elevated risk of having cancer.

21 Claims, 9 Drawing Sheets

METHOD OF DETECTING CANCER AND EVALUATING CANCER PROGNOSIS

RELATED APPLICATION

This application claims priority from U.S. Provisional Application No. 61/039,290, filed Mar. 25, 2008, the subject matter of which is incorporated herein by reference.

FIELD OF INVENTION

The present invention relates generally to methods for detecting cancer and evaluating cancer prognosis in a subject, and more particularly to methods for evaluating cancer prognosis of a subject based on the detected level of pro-prion protein.

BACKGROUND OF THE INVENTION

The normal cellular prion protein (PrP) is a highly conserved, widely expressed, glycophospholinositol (GPI)-anchored cell surface glycoprotein (Prusiner, S. B. (1998) *Proc Natl Acad Sci. USA* 95, 13363-13383; Brockes, J. P. (1999) *Curr Opin Neurobiol.* 9, 571-577). Since its discovery, most studies on PrP have focused on its role in a group of neurodegenerative conditions, known as prion diseases (Prusiner, S. B. (1998) *Proc Natl Acad Sci. USA* 95, 13363-13383; Brockes, J. P. (1999) *Curr Opin Neurobiol.* 9, 571-577). Little is known about PrP outside the nervous system.

The synthesis, processing and transit of PrP to the cell surface are complex and not completely understood (Hegde, R. S. et al., (2003) *Trends Neurosci.* 26, 337-339). Normally, PrP is present in lipid rafts and can function as a signaling molecule (Mouillet-Richard, S. et al., (2000) *Science* 289, 1925-1928; Taylor, D. R. et al., (2006) *Mol Membr Biol.* 23, 89-99). PrP has many binding partners, such as glycosyaminoglycans, copper, laminin receptor, N-CAM, heat shock proteins, dystroglycan, stress-inducible protein, selectin and glypican-1 (Caughey, B. et al., (1994) *J. Virol.* 68, 2135-2141; Brown, D. R. et al., (1997) *Nature* 390, 684-687; Rieger, R. et al., (1997) *Nat Med.* 3, 1383-1388; Schmitt-Ulms, G. et al., (2001) *J Mol Biol.* 314, 1209-1225; Edenhofer, F. et al., (1996) *J. Virol.* 70, 4724-4728; Keshet, G. I. et al., (2000) *J Neurochem.* 75, 1889-1897; Zanata, S. M. et al., (2002) *Embo J.* 21, 3307-3316; Li, C. et al., (2007) *Biochem J.*; Mani, K. et al., (2003) *J Biol Chem.* 278, 38956-38965). PrP also binds Grb2, an adapter protein, lipids and nucleic acids (Lysek, D. A., and Wuthrich, K. (2004) *Biochemistry* 43, 10393-10399; Mahfoud, R. et al., (2002) *J Biol Chem.* 277, 11292-11296; Gabus, C. et al., (2001) *J Mol Biol.* 307, 1011-1021). PrP plays a role in apoptosis in a cell context dependent manner (Chiarini, L. B. et al., (2002) *Embo J.* 21, 3317-3326; Paitel, E. et al., (2003) *J Biol Chem.* 278, 10061-10066; Kuwahara, C. et al., (1999) *Nature* 400, 225-226; Bounhar, Y. et al., (2001) *J Biol Chem.* 276, 39145-39149; Diarra-Mehrpour, M. et al., (2004) *Cancer Res.* 64, 719-727). A recent study found that normal PrP is involved in the proliferation of epithelial cells and in the distribution of junction associated proteins in human enterocytes in vitro and in intestine in vivo (Morel, E. et al., (2008) *PLoS ONE* 3, e3000). However, since the PrP deficient (Prnp$^{-/-}$) mouse is viable and appears to be normal, the physiologic functions of PrP remain an enigma (Bueler, H. et al., (1992) *Nature* 356, 577-582; Westergard, L. et al., (2007) *Biochim Biophys Acta.* 1772, 629-644).

PrP is over-expressed in human gastric cancers (Liang, J. et al., (2006) *Tumour Biol.* 27, 84-91). Expression microarray study found that PRNP is also over-expressed in human colorectal cancers (Antonacopoulou, A. G. et al., (2008) *Anticancer Res.* 28, 1221-1227), and is one of the 25 genes that are over-expressed in pancreatic cancer cell lines (Han, H. et al., (2002) *Cancer Res.* 62, 2890-2896). However, the role PrP plays in tumorigenesis is not clear.

The most common human pancreatic cancer is ductal adenocarcinoma (PDAC), the fourth leading cause of cancer deaths in the U.S. (Jemal, A. et al., (2003) *CA Cancer J Clin.* 53, 5-26). The tumorigenesis of PADC is complex and not completely understood (Li, D. et al., (2004) *Lancet* 363, 1049-1057; Hezel, A. F. et al., (2006) *Genes Dev.* 20, 1218-1249). Evolution of human PDAC correlates with histological changes, characterized by the progression from a flat, columnar epithelium to a papillary, mucinous epithelium with increasing loss of cellular architecture and with nuclear atypia (Hruban, R. H. et al., (2001) *Am J Surg Pathol.* 25, 579-586; Hruban, R. H. et al., (2005) *Methods Mol Med.* 103, 1-13). These precursor lesions are commonly referred to as pancreatic intraepithelial neoplasia (PanIN-1, PanIN-2 and PanIN-3) (Hruban, R. H. et al., (2001) *Am J Surg Pathol.* 25, 579-586; Hruban, R. H. et al., (2005) *Methods Mol Med.* 103, 1-13).

Over the last decade, significant progress has been made in identifying molecular mechanisms underlying PDAC development (Deramaudt, T. et al., (2005) *Biochim Biophys Acta.* 1756, 97-101; Welsch, T. et al., (2007) *Curr Mol Med.* 7, 504-521; Maitra, A. et al., (2008) *Annu Rev Pathol.* 3, 157-188). The most common genetic lesions found in human PDAC are mutations in K-Ras, p53, DAPC-4 (Smad 4) and p16, suggesting that these genes are pivotal in the genesis of human PDAC. This interpretation is supported by studies in transgenic mouse models (Hingorani, S. R. et al., (2005) *Cancer Cell* 7, 469-483; Ijichi, H. et al., (2006) *Genes Dev.* 20, 3147-3160). It was found that mutation in K-Ras in association with additional genetic lesions, such as deletion of p53, p16 or Tgfbr 2 is sufficient to drive PDAC formation (Hingorani, S. R. et al., (2005) *Cancer Cell* 7, 469-483; Ijichi, H. et al., (2006) *Genes Dev.* 20, 3147-3160). However, other growth factor receptors, signal transducing molecules and cell surface molecules have also been implicated in PDAC carcinogenesis (Hezel, A. F. et al., (2006) *Genes Dev.* 20, 1218-1249; Maitra, A. et al., (2008) *Annu Rev Pathol.* 3, 157-188).

SUMMARY

The present invention relates generally to methods for detecting cancer and evaluating cancer prognosis in a subject, and more particularly to methods for evaluating cancer prognosis of a subject based on the detected level of pro-prion protein (pro-PrP). According to one aspect of the present invention, a method is provided for detecting cancer in a subject. One step of the method can include obtaining a bodily sample from the subject. Next, the level of pro-PrP in the bodily sample can be detected. The level of pro-PrP in the bodily sample may then be compared to a control level. An increased level of pro-PrP in the bodily sample as compared to the control level indicates that the subject may have cancer or an elevated risk of having cancer.

According to another aspect of the present invention, a method is provided for detecting pancreatic cancer in a subject. One step of the method can include obtaining a bodily sample from the subject. Next, the level of pro-PrP in the bodily sample can be detected. The level of pro-PrP in the bodily sample may then be compared to a control level. An increased level of pro-PrP in the bodily sample as compared to the control level can indicate that the subject has pancreatic cancer or an elevated risk of having pancreatic cancer.

According to another aspect of the present invention, a method is provided for evaluating the prognosis of a subject having pancreatic cancer. One step of the method can include obtaining a bodily sample from the subject. The bodily sample can comprise a pancreatic secretion selected from the group consisting of pancreatic juice and bile. Next, the level of pro-PrP in the bodily sample can be detected. The level of pro-PrP in the bodily sample may then be compared to a control level. The presence of pro-PrP in the bodily sample may be indicative of a poor prognosis. The poor prognosis can include a median survival time of less than about 1 year.

BRIEF DESCRIPTION OF THE DRAWINGS

FIG. 3A is a diagram of processing of GPI-anchored PrP and the epitopes of the monoclonal antibodies (Mabs) (CHO=N-linked glycans). FIG. 3B is a series of confocal microscopy images showing that WV cells express PrP on the cell surface. All seven PDAC cell lines express varying levels of PrP on the cell surface as well as in the cytoplasm. FIG. 3C is a series of histograms showing the presence of PrP on the cell surface of live PDAC cell lines. BxPC 3 cells appear to have the highest levels of cell surface PrP (BG=background, cells stained with control, irrelevant Mab D7C7);

FIG. 4A shows immunoblots of PrP from WV cells. PrP has a molecular mass of 34 kDa, while PrP from the PDAC cell lines has a molecular mass of 26 kDa. A recombinant PrP (rPrP) produced from $E.\ Coli$ is included as a control and molecular mass marker. FIG. 4B shows immunoblots illustrating treatment of PrP from WV cells with PNGase-F that reduces its molecular mass from 34 kDa to 25.5 kDa, but identical treatment does not change the mobility of PrP from the PDAC cell lines. FIG. 4C shows immunoblots illustrating that PrP from WV cells is sensitive to PI-PLC as shown by the appearance of a smaller PrP species, but PrP from the PDAC cell lines is resistant to PI-PLC. FIG. 4D shows immunoblots illustrating that while PrP from the two PDAC cell lines is sensitive to carboxypeptidase B, but PrP from WV cells is resistant. CD55 from BxPC 3 cells is also resistant to carboxypeptidase B. FIG. 4E shows immunoblots illustrating that a rabbit antiserum specific for the PrP GPI-PSS reacts with recombinant pro-PrP ($rPrP^{23-253}$) but not with mature PrP ($rPrP^{23-231}$). The anti-GPI-PSS antiserum also reacts with pro-PrP from the PDAC cell lines but does not react with the PrP from WV cells;

FIG. 5A is a silver-stained gel showing that a band with molecular mass of 280 kDa is co-immunoprecipitated with Mab 8B4 but not with control Mab D7C7. FIG. 5B is a series of immunoblots showing the co-purification of FLNa with PrP and vice versa. FIG. 5C is a series of confocal images showing co-localization of FLNa (green) and PrP (red) in PDAC cell lines. FIG. 5D is a series of immunoblots showing that PrP and FLNa are present in similar fractions after centrifugation in sucrose gradient. FIG. 5E illustrates an in vitro pull down experiment showing the binding of full-length FLNa to a GST fusion protein, which has the PrP GPI-PSS. Immune complexes were pulled down with GST binding beads and immunoblotted with an anti-FLAG Mab to detect FLNa. FIG. 5F is series of immunblots showing binding of FLNa to pro-PrP but not mature PrP. Anti-PrP Mab 8H4 was used to pull down the immune complexes. The immunoblot was done either with an anti-FLAG Mab or anti-PrP Mab 8H4. FIG. 5G is a series of immunoblots showing competition binding of FLNa to pro-PrP by a PrP-GPI-PSS synthetic peptide. Co-purification of PrP and FLNa in the PDAC cell lysates was carried out in the presence of different concentrations of either a synthetic peptide corresponding to the GPI-PSS (232-250) or a control "scrambled" synthetic peptide. Anti-PrP Mab 8B4 co-immunoprecipitated proteins were then immunoblotted with an anti-FLNa Mab;

FIG. 8A is a series of histograms showing that about 30-40% GPI-anchored PrP on the surface of WV cells is sensitive to PI-PLC. On the other hand, identical treatment of BxPC-3 cells with PI-PLC did not reduce the level of cell surface PrP. FIG. 8B is a series of immunoblots showing that PrP in BxPC-3 cells is no longer present in lipid rafts, but significant amount of flottilin-1 from BxPC-3 cells is still in lipid rafts. Cell lysates were prepared and fractionated in a sucrose gradient as described. Each fraction was immunoblotted with either Mab 8B4 or a Mab specific for flottillin-1, a lipid raft residential protein; FIG. 9A is a series of histograms showing that cell surface PrP on PDAC cell lines reacts with anti-PrP Mabs, 3F4, 11G5, 8H4 and 8F9. The difference in the intensity of the staining is likely due to differences in the affinity of the Mabs. FIG. 9B is a series of confocal microscopy images showing that the anti-PrP-GPI-PSS antiserum reacts with fixed PDAC cells but the control non-immune serum does not react with fixed PDAC cells. FIG. 9C is a series of histograms showing that the anti-PrP-GPI-PSS does not react with live PDAC cells.

DETAILED DESCRIPTION

Figure 1:
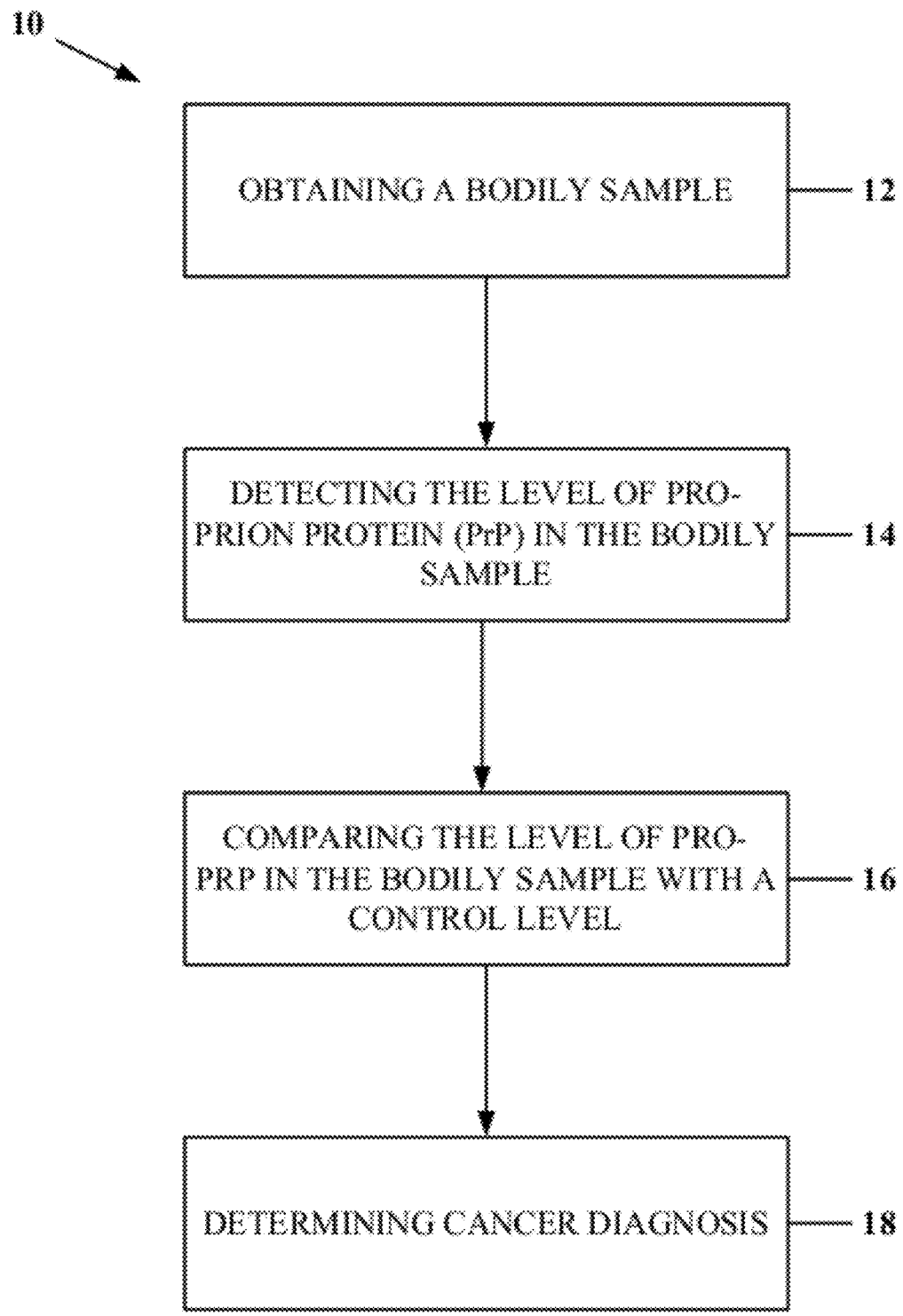
FIG. 1 is a flow diagram illustrating a method for detecting cancer according to one aspect of the present invention.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

In the context of the present invention, the terms "cancer" or "tumor" can refer to any neoplastic growth in a subject, including an initial tumor and any metastases. The cancer can be of the liquid or solid tumor type. Liquid tumors can include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the pancreas, lungs, breasts, prostate, ovaries, colon, kidneys and liver.

As used herein, the terms "cancer cell" or "tumor cell" can refer to cells that divide at an abnormal (i.e., increased) rate. Cancer cells can include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region, sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, meningoma, medulloblastoma, schwannoma and epidymoma.

As used herein, the term "polynucleotide" can refer to oligonucleotides, nucleotides, or to a fragment of any of these, to DNA or RNA (e.g., mRNA, rRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids, i.e., oligonucleotides, containing known analogues of natural nucleotides. Additionally, the term can encompass nucleic acid-like structures with synthetic backbones.

As used herein, the term "polypeptide" can refer to an oligopeptide, peptide, polypeptide, or protein sequence, or to a fragment, portion, or subunit of any of these, and to naturally occurring or synthetic molecules. The terms "polypeptide" can also include amino acids joined to each other by peptide bonds or modified peptide bonds, i.e., peptide isosteres, and may contain any type of modified amino acids. Additionally, the term "polypeptide" can include peptides and polypeptide fragments, motifs and the like, glycosylated polypeptides, and all "mimetic" and "peptidomimetic" polypeptide forms.

As used herein, the term "subject" can refer to any warm-blooded organism including, but not limited to, human beings, rats, mice, dogs, goats, sheep, horses, monkeys, apes, pigs, rabbits, cattle, etc.

As used herein, the terms "detection" or "detecting" are used in the broadest sense and can include both qualitative and quantitative measurements of pro-PrP.

Various known immunoassays may be employed as a pro-PrP detection means. Examples of such immunoassays can include sandwich methods employing a monoclonal antibody and another monoclonal antibody as primary and secondary antibodies, respectively, sandwich methods employing a monoclonal antibody and a polyclonal antibody as primary and secondary antibodies, and sandwich methods employing the polyclonal antibody and a polyclonal antibody as primary and secondary antibodies.

As used herein, the term "antibody" is used in the broadest sense and can include polyclonal antibodies, monoclonal antibodies, and epitope binding antibody fragments thereof so long as they exhibit the desired binding specificity.

As used herein, the terms "monoclonal antibody" or "monoclonal antibodies" can refer to a preparation produced by one type of immune cell that are all clones of a single parent cell typically including identical antibodies directed against a single epitope. The modifier "monoclonal" indicates the character of the antibody and is not to be construed as requiring production of the antibody by any particular method.

As used herein, the terms "polyclonal antibody" or "polyclonal antibodies" can refer to a preparation typically including different antibodies directed against multiple epitopes. The modifier "polyclonal" indicates that character of the antibody as being obtained from a heterogeneous population of antibodies, and is not to be construed as requiring production of the antibody by any particular method.

As used herein, the term "bodily sample" is used herein in its broadest sense and can refer to a biological sample obtained from a subject (e.g., a human) or from components (e.g., tissues) of a subject. The bodily sample may be of any biological tissue or fluid with which pro-PrP may be assayed. For example, the bodily sample can include a "clinical sample", i.e., a sample derived from a subject. Such samples can include, but are not limited to, peripheral bodily fluids, which may or may not contain cells, e.g., blood, urine, plasma, mucous, bile pancreatic juice, supernatant fluid, and serum; tissue or fine needle biopsy samples; and archival samples with known diagnosis, treatment and/or outcome history. Bodily samples may also include sections of tissues, such as frozen sections taken from histological purposes. The term "bodily sample" can also encompass any material derived by processing the bodily sample. Derived materials can include, but are not limited to, cells (or their progeny) isolated from the bodily sample and proteins or nucleic acid molecules extracted from the sample. Processing of the bodily sample may involve one or more of, filtration, distillation, extraction, concentration, fixation, inactivation of interfering components, addition of reagents, and the like.

As used herein, the terms "normal" and "healthy" are used interchangeably. The terms can refer to a subject or group of subjects who have not shown any cancer symptoms or do not have an elevated risk of having cancer. In certain aspects of the present invention, normal subjects may have similar sex, age, and body mass index as compared with a subject from which a bodily sample to be tested was obtained.

As used herein, the terms "control" or "control sample" can refer to one or more bodily samples isolated from an subject or group of subjects that are normal (i.e., healthy). A control sample can also refer to a bodily sample isolated from a subject or group of subjects diagnosed with a specific stage of cancer. The terms can also refer to the compilation of data derived from samples of one or more subjects classified as normal, or one or more subjects diagnosed with cancer, a specific stage of cancer, or one or more subjects having undergone treatment of cancer.

As used herein, the terms "labeled", "labeled with a detectable agent", and "labeled with a detectable moiety" may be used interchangeably. These terms may be used to specify that an entity (e.g., an antibody) can be visualized, for example, following binding to another entity (e.g., a protein). The detectable agent or moiety can be selected such that it generates a signal, which can be measured and whose intensity is related to the amount of bound entity. Methods for labeling polypeptides are well-known in the art. Labeled polypeptides can be prepared by incorporation of or conjugation to a label that is directly or indirectly detectable by spectroscopic, photochemical, biochemical, immunochemical, electrical, optical, or chemical means. Examples of detectable agents can include, but are not limited to, various ligands, radionuclides, fluorescent dyes, chemiluminescent agents, microparticles, enzymes, calorimetric labels, magnetic labels, and haptens. Detectable moieties can also include biological molecules, such as molecular beacons and aptamer beacons.

The present invention relates generally to methods for detecting cancer and evaluating cancer prognosis in a subject, and more particularly to methods for evaluating cancer prognosis of a subject based on the detected level of pro-prion protein (pro-PrP). Pro-PrP as contemplated by the present invention is encoded by the PRNP gene. PRNP is over-expressed in various cancer cell lines, such as pancreatic cancer cell lines, endocrine tumor cell lines, colorectal cancer cell lines, and gastric cancer cell lines, but the significance is unknown. Normal PrP is a glycoprotein that is attached to the plasma membrane by a C-terminally linked glycosyl phosphatidylinositol anchor (GPI). Pro-PrP retains its C terminal GPI anchor peptide signal sequence (GPI-PSS), but is not glycosylated nor is it GPI anchored to the plasma membrane. Without being bound by theory, it is believed that pro-PrP is instead inserted into the cell surface membrane using the GPI-PSS as a trans-membrane anchoring domain.

Pro-PrP GPI-PSS also has a filamin A (FLNa) binding motif, which allows it to bind FLNa. FLNa is an actin binding protein that acts as an integrator of cell mechanics and signaling and is known to participate in the anchoring of membrane proteins for the actin cytoskeleton. Remodeling of the cytoskeleton is central to the modulation of cell shape and migration. It was found that in cancer cells expressing pro-PrP, the binding of pro-PrP to FLNa can perturb the normal function of FLNa and contribute to the growth, proliferation, and metastases of the cancer cells. Moreover, it was found that the expression level of pro-PrP in a bodily sample (e.g., blood, pancreatic juice) obtained from a subject can be measured to determine if the subject has a cancer or has an elevate risk of a cancer that is associated with pro-PrP expression.

Additionally, it has been found that expression of pro-PrP in subjects with certain cancers, such as pancreatic ductal adenocarcinoma (PDAC), is associated with shorter median survival time.

FIG. 1 is a flow diagram illustrating a method 10 for detecting cancer in a subject in accordance with an aspect of the present invention. By way of example, the method 10 can be used to detect pancreatic cancer in a subject, such as pancreatic adenomas, adenocarcinomas, gastrinomas, somatostatinomas, insulinomas, glucagonomas of the pancreas, and ductal adenocarcinomas, which arise from the progression of lesions that occur in the pancreatic ducts.

As shown in FIG. 1, the method 10 at Step 12 can include obtaining a bodily sample from the subject. The subject can be an apparently healthy subject or, alternatively, a subject at risk for having cancer. "Apparently healthy", as used herein, can refer to subjects who have not previously been diagnosed as having any signs or symptoms indicating the presence of cancer, a history of cancer, or evidence of cancer. Apparently, healthy subjects may not otherwise exhibit symptoms of cancer. In other words, such subjects, if examined by a medical professional, would be characterized as healthy and free of symptoms of cancer.

Subjects at risk for cancer can exhibit and/or be exposed to any one or combination of risk factors including, but not limited to, certain food types (e.g., those containing acrylamide or heterocyclic amines), genetics (e.g., family history, BRCA1, etc.), hormone use (e.g., diethylstilbestrol), radiation, tobacco use, weight, physical inactivity, and workplace environment (e.g., asbestos or benzene exposure). For example, subjects at risk for pancreatic cancer can exhibit any one or combination of risk factors including, but not limited to, pain in the upper abdomen that radiates to the back, loss of appetite, nausea, vomiting, significant weight loss, jaundice, Trousseau sign, over 60 years of age, male gender, smoking, diabetes mellitus, expression of certain blood group antigens, such as type B or type AB, and African-American ethnicity. Techniques for assessing cancer risk factors are known in the art.

The bodily sample can include a peripheral bodily fluid. For example, the bodily sample can comprise fresh blood, stored blood (e.g., in a blood bank), or a blood fraction. The bodily sample may be a blood sample expressly obtained for the assay(s) of the present invention or, alternatively, a blood sample obtained for another purpose, which can be sub-sampled for the present invention. Bodily samples can be obtained using standard clinical procedures. In one example of the present invention, the bodily sample can comprise a pancreatic secretion, such as pancreatic juice or bile. The pancreatic secretion can be obtained using gastroenterologic techniques known in the art, such as the intraductal sampling technique.

Bodily samples can be pretreated as necessary by dilution in an appropriate buffer solution, heparinized, concentrated if desired, or fractionated by any number of methods including, but not limited to, ultracentrifugation, fractionation by fast performance liquid chromatography, precipitation with dextran sulfate, or other known methods. Any number of standard aqueous buffer solutions employing one or a combination of buffers, such as phosphate, Tris, or the like, at physiological pH can also be used.

Figure 3:
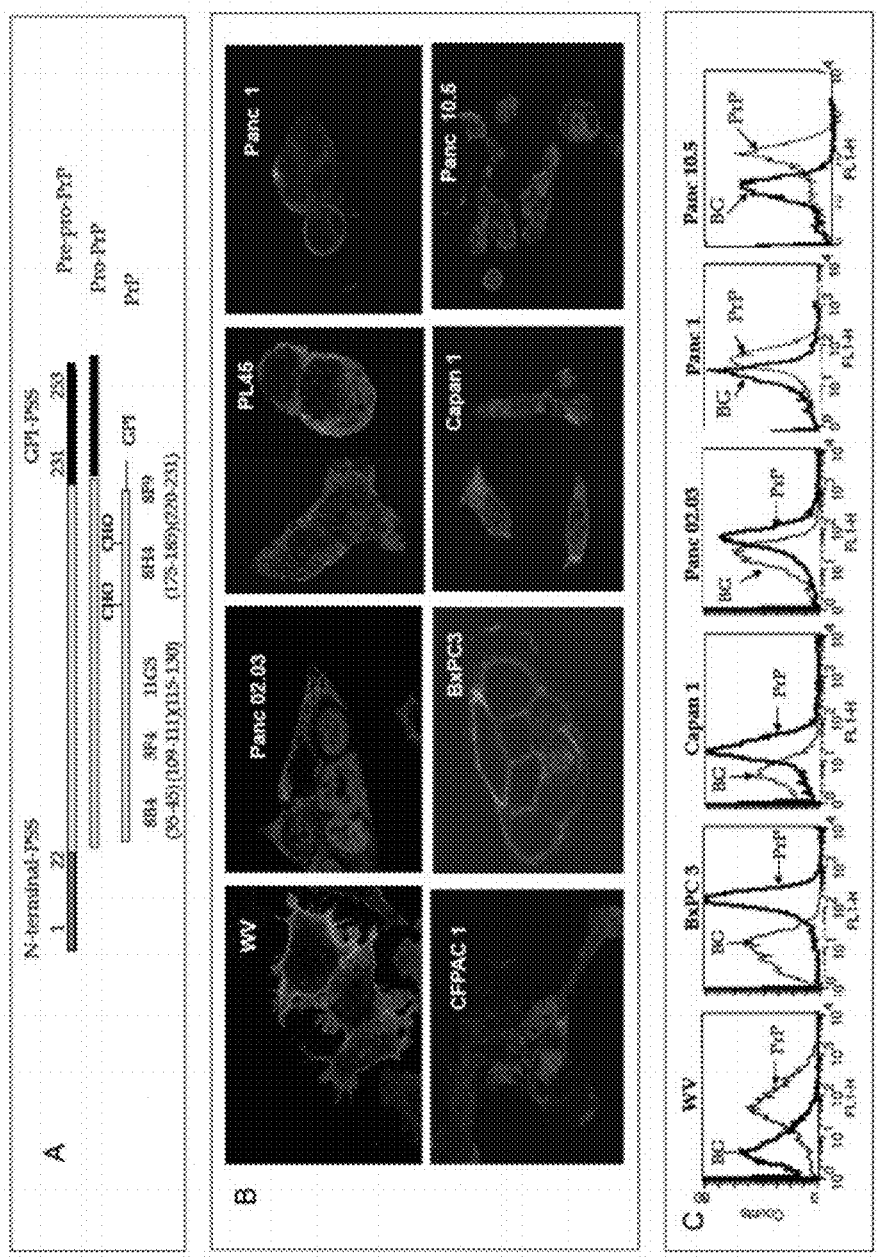
FIGS. 3A-C illustrate expression of prion protein (PrP) in pancreatic ductal adenocarcinoma (PDAC) cell lines.

After obtaining the bodily sample from the subject at Step 14, the level of pro-PrP in the bodily sample can be detected. Human PrP is synthesized as a 253 amino acid long pre-pro-PrP (FIG. 3A). The N-terminus has a leader signal sequence, and the C-terminus end has the GPI-PSS. These sequences are removed in the endoplasmic reticulum and are absent from mature PrP. Thus, the level of pro-PrP in the bodily sample can be detected by contacting the bodily sample with a capture moiety that specifically binds to pro-PrP, and not mature PrP. For example, the capture moiety can bind to the GPI-PSS of pro-PrP having the amino acid sequence of SEQ ID NO: 1. The capture moiety can be used in any one or combination of known biochemical assays or techniques, such as ELISA and Western blots, mass spectroscopy (MS) (e.g., LC/ESI/MS/MS), and chromatography (e.g., HPLC, affinity column, etc.).

In one example of the method 10, the level of pro-PrP can be detected using a sandwich ELISA that includes an immobilized capture moiety that specifically binds to pro-PrP, and not mature PrP. The immobilized capture moiety can be a monoclonal antibody or fragment thereof that specifically binds to pro-PrP. For example, monoclonal antibodies of the present invention can be selected that are immunoreactive with or capable of binding to a GPI-PSS of pro-PrP having the amino acid sequence of SEQ ID NO: 1. Additionally or optionally, the immobilized capture moiety can comprise a protein or small molecule that binds to pro-PrP, such as FLNa or a GPI-PSS binding fragment thereof. It will be appreciated that an immobilized capture moiety can also comprise a polyclonal antibody that specifically binds to pro-PrP, and not mature PrP.

Monoclonal antibodies that are capable of binding to a GPI-PSS of pro-PrP can be derived from any known monoclonal antibody-generating species, such as mice. The monoclonal antibodies can be produced by known monoclonal antibody production techniques. Typically, monoclonal antibodies are prepared by recovering spleen cells from immunized animals with the protein of interest and immortalizing the cells in conventional fashion, for example, by fusion with myeloma cells or by Epstein-Barr virus transformation, and screening for clones expressing the desired antibody (see, e.g., Kohler and Milstein Eur. *J. Immunol.* 6:511 (1976)). Monoclonal antibodies, or the epitope-binding region of a monoclonal antibody, may alternatively be produced by known recombinant methods.

By way of example, where the epitope of interest is a GPI-PSS of pro-PrP, the monoclonal antibody can be a murine monoclonal antibody that is generated by immunizing "knock out" mice with recombinant normal mouse cellular protein (i.e., pro-PrP containing SEQ ID NO: 1). Spleen cells (antibody-producing lymphocytes of limited life span) from the immunized mice can then be fused with non-producing myeloma cells (tumor lymphocytes that are "immortal") to create hybridomas. The hybridomas can then be screened for the production of antibody specific to a GPI-PSS of pro-PrP and the ability to multiply indefinitely in tissue culture. These hybridomas can then be propagated to provide a permanent and stable source for the specific monoclonal antibodies.

The capture moiety can be immobilized on a solid phase by insolubilizing the capture moiety before the assay procedure, as by adsorption to a water-insoluble matrix or surface (see, e.g., U.S. Pat. No. 3,720,760) or non-covalent or covalent coupling, for example, using glutaraldehyde or carbodiimide cross-linking, with or without prior activation of the support with, e.g., nitric acid and a reducing agent as described in U.S. Pat. No. 3,645,852 or in Rotmans et al., *J. Immunol. Methods* 57:87-98 (1983), or afterward, such as by immunoprecipitation.

The solid phase used for immobilization may be any inert support or carrier that is essentially water insoluble and useful in immunometric assays, including supports in the form of, for example, surfaces, particles, porous matrices, etc. Examples of commonly used supports include small sheets, Sephadex, polyvinyl chloride, plastic beads, and assay plates or test tubes manufactured from polyethylene, polypropylene, polystyrene, and the like, including 96-well micro-titer plates and 384-well micro-titer well pates, as well as particulate materials, such as filter paper, agarose, cross-linked dextran, and other polysaccharides. Alternatively, reactive water-insoluble matrices, such as cyanogen bromide-activated carbohydrates and the reactive substrates described in U.S. Pat. Nos. 3,969,287; 3,691,016; 4,195,128; 4,247,642; 4,229,537; and 4,330,440 may be employed for capture moiety immobilization. In one example, immobilized capture moieties can comprise immobilized monoclonal antibodies that specifically bind to pro-PrP and that are coated on a micro-titer plate, and in particular a multi-well micro-titer plate that can be used to analyze several samples at one time (e.g., a microtest 96-well ELISA plate).

The solid phase can be coated with the capture moiety, which may be linked by a non-covalent or covalent interaction or physical linkage as desired. Techniques for attachment include those described in U.S. Pat. No. 4,376,110 and the references cited therein. If covalent binding is used, the plate or other solid phase can be incubated with a cross-linking agent together with the capture reagent under conditions well known in the art.

Commonly used cross-linking agents for attaching capture moieties, such as monoclonal antibodies to a solid phase substrate can include, e.g., 1,1-bis(diazoacetyl)-2-phenylethane, glutaraldehyde, N-hydroxysuccinimide esters, esters with 4-azidosalicylic acid, homobifunctional imidoesters, including disuccinimidyl esters, such as 3,3'-dithiobis(succinimidylpropionate), and bifunctional maleimides, such as bis-N-maleimido-1,8-octane. Derivatizing agents, such as methyl-3-[(p-azidophenyl)dithio]propioimidate can yield photoactivatable intermediates capable of forming cross-links in the presence of light.

If micro-titer well plates (e.g., 96-well plates or 384-well plates) are utilized, they can be coated with affinity-purified capture moieties (typically diluted in a buffer) at, for example, room temperature and for about 2 to about 3 hours. The plates may be stacked and coated long in advance of the assay itself, and then the assay can be carried out simultaneously on several samples in a manual, semi-automatic, or automatic fashion.

The coated plates can then be treated with a blocking agent that binds non-specifically to and saturates the binding sites to prevent unwanted binding of pro-PrP to the excess sites on the wells of the plate. Examples of appropriate blocking agents for this purpose can include, e.g., gelatin, bovine serum albumin, egg albumin, casein, and non-fat milk.

After coating and blocking, the bodily sample comprising pro-PrP can be added to the immobilized phase. The bodily sample can be appropriately diluted with, for example, a lysis buffer (e.g., phosphate-buffered saline (PBS) with 1% Nonidet P-40, 0.5% sodium deoxycholate, 5 mM EDTA, and pH 8.0).

For sufficient sensitivity, the amount of the bodily sample added to the immobilized capture moieties can be such that the immobilized capture moieties are in molar excess of the maximum molar concentration of pro-PrP anticipated in the bodily sample after appropriate dilution of the sample. This anticipated level depends mainly on any known correlation between the concentration levels of pro-PrP in the particular bodily sample being analyzed with the clinical condition of the subject.

The conditions for incubation of the bodily sample and immobilized capture moieties are selected to maximize sensitivity of the assay and to minimize dissociation. Preferably, the incubation is accomplished at fairly constant temperatures, ranging from about 0° C. to about 40° C., such as room temperature (e.g. about 25° C.). The time for incubation depends primarily on the temperature, being generally no greater than about 10 hours to avoid an insensitive assay. For example, the incubation time can be from about 0.5 to 3 hours, and particularly about 1.5 to about 3 hours at room temperature to maximize binding to the capture moieties.

Following contact of the bodily sample with the immobilized capture moieties, the bodily sample can be separated (e.g., by washing) from the immobilized capture moieties to remove uncaptured pro-PrP. The solution used for washing is generally a buffer ("washing buffer") with a pH determined using the considerations and buffers typically used for the incubation step. The washing may be done, for example, three or more times. The temperature of washing is generally from refrigerator temperature to moderate temperatures, with a constant temperature maintained during the assay period, typically from about 0° C. to about 40° C. Optionally, a cross-linking agent or other suitable agent may be added at this stage to allow the now-bound pro-PrP to be covalently attached to the capture moieties if there is any concern that the captured pro-PrP may dissociate to some extent in the subsequent steps.

Following separation of the uncaptured bodily sample, the immobilized capture moieties and captured pro-PrP can be contacted with detection moieties (or epitope binding fragments thereof) that are capable of binding to free binding epitopes on the captured pro-PrP. For example, the detection moieties can comprise labeled monoclonal or polyclonal antibodies capable of binding to free binding epitopes on the captured pro-PrP. The immobilized capture moieties and captured pro-PrP can be contacted with the detection moieties at a temperature, for example, of about 20° C. to about 40° C. A molar excess of the detection moieties with respect to the maximum concentration of free binding epitopes expected can be added to the plate after it is washed.

The detection moieties can be labeled with any detectable agent that does not interfere with the binding of the detection moieties to free binding epitopes on the bound pro-PrP. Examples of detectable agents can include labels known for use in immunoassays, including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores, such as rare earth chelates or fluorescein and its derivatives, rhodamine and its derivatives, dansyl, umbelliferone, luceriferases, e.g., firefly luciferase and bacterial luciferase (e.g., U.S. Pat. No. 4,737,456), luciferin, 2,3-dihydrophthalazinediones, horseradish peroxidase (HRP), alkaline phosphitase, β-galactosidase, glucoamylase, lysozyme, saccharide oxidases, e.g., glucose oxidase, galactose oxidase, and glucose-6-phosphate dehydrogenase, heterocyclic oxidases, such as uricase and xanthine oxidase, coupled with an enzyme that employs hydrogen peroxide to oxidize a dye precursor, such as HPP, lactoperoxidase, or microperoxidase, biotin/avidin, biotin/streptavidin, biotin/ Streptavidin-β-galactosidase with MUG, spin labels, bacteriophage labels, stable free radicals, and the like. Conventional methods are available to bind these labels covalently to proteins or polypeptides. For instance, coupling agents, such as dialdehydes, carbodiimides, dimaleimides, bis-imidates, bis-diazotized benzidine, and the like may be used to tag the antibodies with the above-described fluorescent, chemiluminescent, and enzyme labels, e.g., U.S. Pat. Nos. 3,940,475 (fluorimetry) and 3,645,090 (enzymes); Hunter et al. *Nature* 144:945 (1962); David et al. *Biochemistry* 13:1014-1021 (1974); Pain et al. *J. Immunol Methods* 40:219 230 (1981); and Nygren J. *Histochem and Cytochem* 30:407-412 (1982).

The conjugation of such label, including the enzymes, to the antibody is a standard manipulative procedure for one of ordinary skill in immunoassay techniques. See, e.g., O'Sullivan et al. "Methods for the Preparation of Enzyme-antibody Conjugates for Use in Enzyme Immunoassay," in *Methods in Enzymology*, ed. J. J. Langone and H. Van Vunakis, Vol. 73 (Academic Press, New York, N.Y., 1981), pp. 147-166.

Following the addition of detection moieties, the amount of bound detection moieties is determined by removing excess unbound labeled detection moieties by washing and then measuring the amount of the attached label using a detection method appropriate to the label. In the case of enzymes, for example, the amount of color developed and measured can be a direct measurement of the amount of pro-PrP present in the bodily sample.

After determining the level of pro-PrP in the bodily sample at Step 16, the level of detected pro-PrP can be compared to a control level. The control level can be based upon the level of pro-PrP in a comparable bodily sample (or samples) obtained from a control population (e.g., the general population) or a select population of subjects. For example, the select population may be comprised of apparently healthy subjects or from subjects at risk of developing cancer.

The control level can be related to the value used to characterize the level of pro-PrP obtained from the subject. For example, if the level of pro-PrP is an absolute value, such as the units of pro-PrP per ml of blood, the control level can also based upon the units of pro-PrP per ml of blood in subjects of the general population or a select population. Similarly, if the level of pro-PrP is a representative value, such as an arbitrary unit obtained from an ELISA, the control level can also be based on the representative value.

The control level can take a variety of forms. For example, the control level can be a single cut-off value, such as a median or mean. The control level can be established based upon comparative groups, such as where the risk in one defined group is double the risk of another defined group. The control level can also be divided equally (or unequally) into groups, such as a low-risk group, a medium-risk group, and a high-risk group, or into quadrants, the lowest quadrant being subjects with the lowest risk the highest quadrant being subjects with the highest risk.

Control levels of pro-PrP in bodily samples, for example, can be obtained (e.g., mean levels, median levels, or "cut-off" levels) by assaying a large sample of subjects in the general population or a select population and then using a statistical model, such as the predictive value method for selecting a positivity criterion or receiver operator characteristic curve that defines optimum specificity (highest true negative rate) and sensitivity (highest true positive rate), as described in Knapp, R. G. and Miller, M. C. (1992): *Clinical Epidemiology and Biostatistics*, William and Wilkins, Harual Publishing Co. (Malvern, Pa.).

Depending upon the level or value of detected pro-PrP when compared to the control level, a determination or diagnosis can be made as to whether the subject has cancer or is at an elevated risk of having cancer at Step 18. The absence of substantially any detectable signal can be indicative of the absence of substantially any cancer. Conversely, the measurement of a detectable signal can be indicative of the presence of cancer. For example, a subject may have pancreatic cancer or be at an elevated risk of having pancreatic cancer where the method 10 reveals an increased level of pro-PrP in a bodily sample as compared to the control level.

Figure 2:
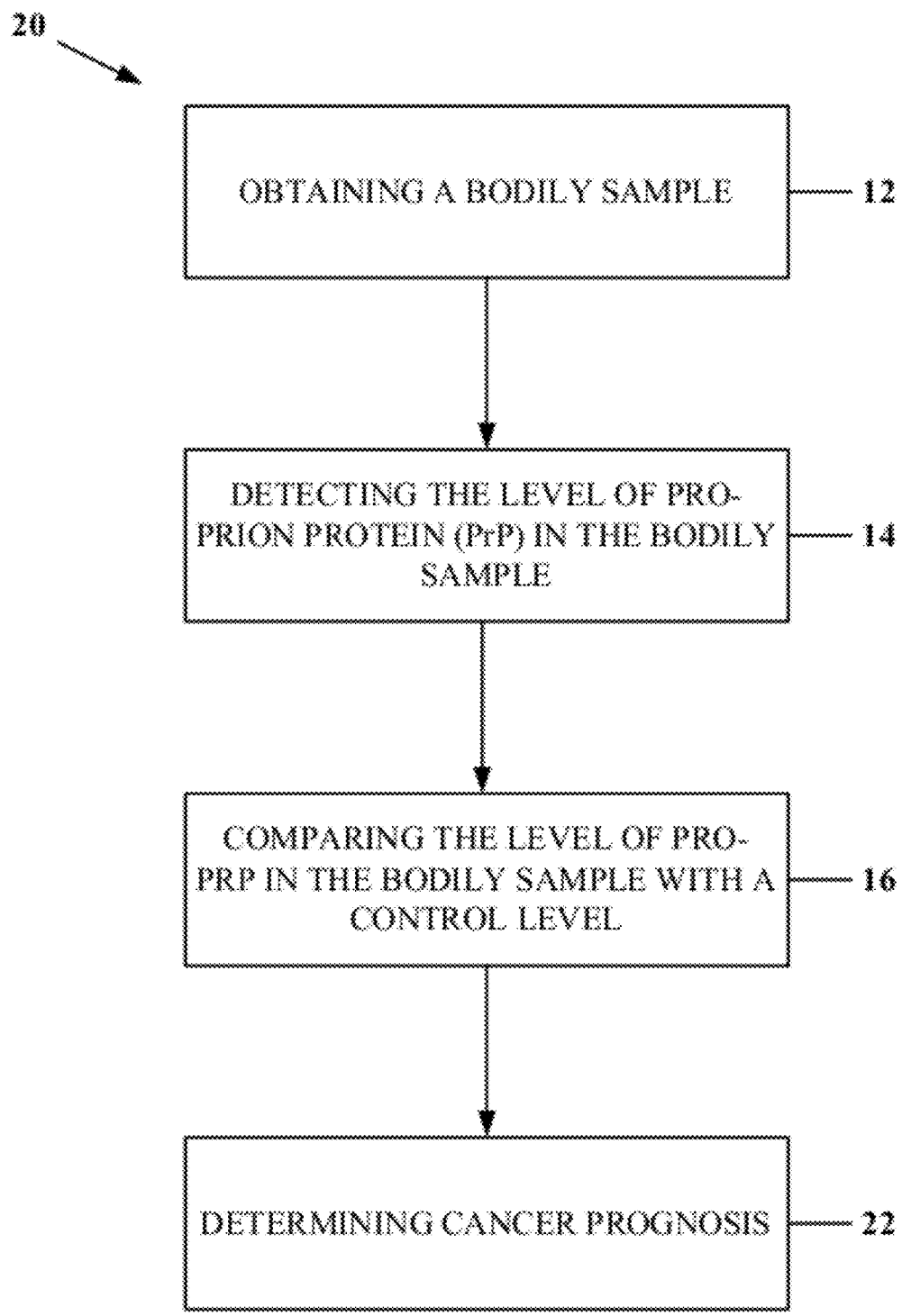
FIG. 2 is a flow diagram illustrating a method for evaluating the prognosis of a subject having pancreatic cancer according to another aspect of the present invention.

FIG. 2 is a flow diagram illustrating another aspect of the present invention. In FIG. 2, a method 20 is provided for evaluating the prognosis of a subject having pancreatic cancer. The steps of the method 20 are similar to Steps 12-16 of the method 10 (FIG. 1), except where described below. For example, a bodily sample, such as a pancreatic secretion (e.g., pancreatic juice or bile) can be obtained from the subject at Step 12 (FIG. 2). At Step 14, the level of pro-PrP can be detected using a sandwich ELISA. As described above, the bodily sample can be contacted with a capture moiety that specifically binds to pro-PrP, and not PrP, such as a monoclonal antibody that binds to a GPI-PSS of pro-PrP having SEQ ID NO: 1. At Step 16, the level of detected pro-PrP in the bodily sample can be compared to a control level.

After comparing the detected level of pro-PrP with the control level, the prognosis of the subject can be determined at Step 22. As used herein, the term "prognosis" can be defined as a prediction of a probable course and/or outcome of a cancer (e.g., pancreatic cancer). One measure of a subject's prognosis can include median survival time. "Median survival time" can refer to the time from either diagnosis or treatment at which half of the subjects with a given cancer are found to be, or expected to be, still alive. A poor prognosis may indicate that a subject's median survival time is less than about 5 years, less than about 3 years, and, for example, less than about 1 year. At Step 22 of the method 20, the presence of pro-PrP in the bodily sample may be indicative of the subject having a poor prognosis. Where, for example, pro-PrP is detected in a pancreatic secretion obtained from a subject, a determination may be made that the subject has a poor prognosis; that is, the median survival time of the subject may be less than about 1 year.

The following example is intended to illustrate embodiments now known for practicing the invention, but the invention is not to be considered limited to this example.

EXAMPLE

Methods

Cell lines, Mabs and reagents: all the PDAC cell lines, BxPC 3, Panc 02.03, Capan 1, PL45, CFPAC 1, Panc 1 and Panc 10.05 were obtained from A.T.C.C. WV is a human neuroblastoma cell line that was originally generated in the laboratory of Dr. R. Petersen (Petersen, R. B. et al., (1996) *J Biol Chem.* 271, 12661-12668). Anti-PrP Mabs 8H4, 11G5, and 8B4 were generated in our laboratory (Zanusso, G. et al., (1998) *Proc Natl Acad Sci.* USA 95, 8812-8816; Li, R. et al., (2000) *J Mol Biol.* 301, 567-573). The rabbit anti-PrP-GPI-PSS antiserum was generated by immunizing rabbits repeatedly with a synthetic peptide corresponding to the GPI-PSS of pro-PrP (SEQ ID NO: 1) in CFA. The antiserum was first absorbed with mature rPrP23-231 and then purified with PrP-GPI-PSS affinity chromatography. All other Mabs and reagents were purchased from commercial sources and used according to the recommendations of the vendors. Mature PrP, pro-PrP and PrP-GPI-PSS GST fusion proteins were prepared using conventional techniques.

Capan-1 was cultured in Isocove's Modified Dulbecco's Eagle Medium (IMDM) supplemented with 1.5 g/L Sodium Bicarbonate and 20% fetal bovine serum (FBS). PL-45 was cultured in high glucose Dulbecco's Modified Eagle Medium (DMEM) supplemented with 1.5 g/L Sodium Bicarbonate and 10% FBS. Panc.02.03 was culture in RPMI 1640 supplemented with 1.5 g/L Sodium Bicarbonate, 15% FBS, 1% Sodium Pyruvate, 1 mM Hepes, 20 U insulin, and 4.5 g/L Glucose. BxPC3 was cultured in RPMI1640 supplemented with 1.5 g/L Sodium Bicarbonate, 10% FBS, 1% Sodium Pyruvate, 1 mM Hepes, and 4.5 g/L Glucose. WV was cultured in RPMI 1640 supplemented with 10% FBS, 1% Sodium Pyruvate, 1 mM Hepes.

Anti-PrP Mabs 8H4 and 8B4 were generated in our laboratory and have been characterized extensively. Anti-CD55 Mab was purchased from BD Bioscience (San Jose, Calif.). Anti-FLNa A Mab, horseradish peroxidase (HRP) conjugated goat anti-human IgG Fc specific antibody and mouse anti-actin Mab were purchased from Chemicon (Temecula, Calif.). Anti-tyrosine-phosphorylated protein, anti-PAK, anti-phosphorylated PAK, anti-LIMK1, anti-LIMK2, anti phosphorylated LIMK1/2, anti-cofilin, anti-phosphorylated cofilin, and anti-chronophin antibodies were purchased from Cell Signaling Technology (Beverly, Mass.). Anti-CD55, Anti-ROCK1 and anti-ROCK2 antibodies were purchased from BD Biosciences (San Jose, Calif.). Fluorescein isothiocyanate (FITC)-labeled goat anti-mouse IgG antibody was purchased from Southern Biotech (Birmingham, Ala.). Texas red-conjugated phalloidin and 4',6-diamidino-2-phenylidole, dialactate, (DAPI) were purchased from Invitrogen (Carlsbad, Calif.). Protein G-agarose beads were purchased from Roche (Indianapolis, Ind.). PNGase F was purchased from New England BioLabs (Beverly, Mass.). Profound CO-IP kit, EDTA-free protease inhibitor cocktail, dimethyl suberimidaet.2HCL (DMS) and SUPERSIGNAL West Femto kit were purchased from Pierce (Rock, Ill.). Bio-Rad protein assay kit and silver stain plus kit were purchased from Bio-Rad (Hercules, Calif.). Phenylmethanesulfonyl fluoride (PMSF), Triton x-100, Tween-20, and phospholipase C (PI-PLC) were purchased from Sigma (St. Louis, Mo.). Carboxypeptidases B and Y were purchased from Worthington Biochemical Corporation (Lakewood, N.J.).

Immunofluorescence staining for confocal microscopy: tumor cell lines were cultured in poly-D-lysine-coated glass bottom Petri dishes (MatTek, Ashland, Mass.) overnight. Cells were then rinsed 3× with ice cold PBS and fixed in 4% paraformaldehyde for 15 min. at 20° C. PrP or FLNa was detected with anti-PrP Mab 8H4 or anti-FLNa Mab PM6/317 (0.01 μg/μl). Bound antibody was detected with an Alexa Fluor 488 nm-conjugated goat anti-mouse Ig specific antibody. Nuclei were stained with DAPI. To detect FLNa in PrP "down-regulated" cells, cells were fixed and then permeablized with 0.3% Triton X-100 in PBS for 10 min. at 20° C. The other steps were carried out as described in above. F-actin was detected with Texas Red-conjugated phalloidin. Samples were analyzed on a LSM 510 META confocal microscope at The Case Comprehensive Cancer Center, Image Core Facility.

In vitro proliferation: identical numbers ($1 \times 10^4$) of cells were cultured in vitro in 24 well plates in triplicate. At different days after culture, the numbers of cells in each well were counted. The results presented were the mean of the triplicate wells +/−S.D. at each time point. These results were confirmed with three independently generated control and PrP "down-regulated" cell lines.

In vitro invasion assay: in vitro invasion assays were performed in Bio-Coat Growth Factor Reduced MATRIGEL Invasion chamber (BD Bioscience) using protocols provided by the supplier. The results presented were the mean of the triplicate wells +/−S.D. These results were confirmed with three independently generated control and PrP down-regulated cell lines.

Growth of tumor cells in nude mice: Tumor cells were grown in vitro to 90% confluence, washed ×2 in cold PBS buffer, harvested, washed with cold PBS ×3, counted and kept on ice prior to injection. 1×10⁷ cells in 0.1 ml were injected subcutaneously into the back of nude mice. In the BxPC-3 experiment, at 21 days after implantation, the tumor mass from each individual mouse was surgically removed and weighed. In the Panc 02.03 experiment, at various times after tumor cell implantation (5 mice/group/tumor cell line), the length and width of the tumor were measured using a digital caliper. The results presented were the mean of the weights of the tumors or the length×width²/2 of the tumor +/−S.D. These results were confirmed with three independently generated control and PrP down-regulated cell lines.

Tissue samples and immunohistochemical staining: Paraffin-embedded blocks of 83 surgically resected primary infiltrating pancreatic ductal adenocarcinomas resected between 2001 and 2006 were collected from the Surgical Pathology Files of University Hospitals of Cleveland. Clinical and pathological data were obtained from detailed chart review, which included age, gender, race, tumor size, tumor location, lymph node metastasis status, and histological subtype of the invasive carcinoma. The H and E stained slides from each case were visually inspected by light microscopy and representative sections were selected for immunostaining.

Flow cytometry and confocal microscopy: To detect cell surface PrP in living tumor cell lines, cells were seeded in 25 cm² flask 12 hours before experiment, rinsed with ice cold DPBS once, and then released by treatment with Trypsin/EDTA. Mabs 8H4 or D7C7 (0.01 µg/µl) were then added to the cell suspensions at 4° C. After washing, bound antibody was detected by an Alexa Fluor 488 nm-conjugated goat anti-mouse Ig specific antibody and then analyzed in a BD FACS flow cytometer. To detect PrP or FLNa expression by confocal microscopy, tumor cell lines were cultured in poly-D-lysine-coated glass bottom Petri dish (MatTek, Ashland, Mass.) overnight. Cells were then rinsed 3× with ice cold DPBS and fixed in 4% paraformaldehyde for 15 minutes at 20° C. PrP or FLNa was detected with anti-PrP or anti-FLNa Mabs (0.01 µg/µl). Bound antibody was further detected with an Alexa Fluor 488 nm-conjugated goat anti-mouse Ig specific antibody. Nuclei were stained with DAPI. To detect FLNa in PrP down-regulated tumor cells, cells were fixed and then permeablized with 0.3% Triton X-100 in PBS for 10 minutes at 20° C. The other steps were carried out as described earlier. To detect change in tyrosine phosphorylated protein (p-tyr), tumor cells were prepared and treated as described in above, an anti-p-tyrosine antibody was added to the cells, and incubated overnight at 4° C. as suggested by the provider of the antibody. Bound antibody was detected with an Alexa Fluor 488 nm-conjugated goat an anti-mouse Ig antibody. Nuclei were stained with DAPI. F-actin was detected with a Texas Red-conjugated Phalloidin.

PI-PLC treatment and flow cytometry analysis of live cells: Tumor cells were seeded overnight as described. The next day, cells were first washed 3 times with ice-cold DPBS, and then treated with trypsin/EDTA to prepare a single cell suspension of the tumor cells. After washing twice with DPBS, cells were incubated with PI-PLC (500× dilution of 1 U) at 37° C. for one hour. At the end of the incubation, cells were washed twice with DPBS and then stained with control antibody or 8H4 as described.

For staining of live BxPC3 and Panc 02.03 cells with rabbit anti-PrP-GPI-PSS serum, single cell suspensions of the tumor cells were prepared as described and then incubated with either a rabbit non-immune serum (1:100) or affinity purified anti-PrP-GPI-PSS serum. An Alexa Fluor 488 nm conjugated donkey anti-Rabbit antibody was used to detect bound rabbit antibody.

For staining of tumor cells with rabbit anti-PrP-GPI-PSS serum for confocal microscopy analysis, tumor cells were seeded overnight, washed 3 times with ice-cold DPBS, then fixed with 4% PFA for 15 minutes at 21° C. Subsequently, tumor cells were washed 3× with PBST, and then incubated with either the rabbit non-immune serum (1:100) or the affinity purified anti-PrP-GPI-PSS serum for 1 hour at 21° C. Bound primary antibody was detected with an Alexa Fluor 488 nm conjugated donkey anti-rabbit antibody.

Immunoblotting and enzymatic treatment of PrP from various tumor cell lines: cell lysates were prepared in lysis buffer containing 20 mM Tris (pH7.5), 150 mM NaCl, 1 mM EDTA, 1 mM EGTA, 1% Triton X-100, 2.5 mM sodium pyrophosphate, 1 mM β-glycerolphosphate, 1 mM Na₃VO₄. 1 mM PMSF, and EDTA-free protease inhibitor cocktail was added just before cell lysis. PrP was affinity purified by Mab 8B4-conjugated beads, eluted and neutralized to pH 7.5 as described (Pan, T. et al., *J Clin Microbiol.* 43(3): 1118-1126, 2005). Purified PrP was subjected to carboxypeptidases or PNGase-F treatment followed by PI-PLC treatment according to the protocols provided by the providers. After treatment, samples were separated on SDS-PAGE and immunoblotted with an anti-PrP antibody. Briefly, 2 U PNGase F was added to 20 µl of eluted and neutralized PrP. 0.375 U PI-PLC was added to 20 ul PNGase F treated PrP. 1 U carboxypeptidases B or Y were added to 20 µl of eluted and neutralized PrP at 20° C. for different periods of time.

Sucrose gradient fractionation: Cell lysates prepared as described were mixed with an equal volume of ice-cold 80% sucrose in MES buffer [25 mM 2-(4-Morpholino) ethane sulfonic acid pH 6.5, 150 mM NaCl, 5 mM EDTA]. Two ml of 40% sucrose/cell lysate was transferred to a 5 ml Ultra-Clear centrifuge tubes (Beckman, Fullerton, Calif.) on ice. 2 ml ice-cold 30% sucrose in MES buffer was placed on top. 1 ml ice-cold 5% sucrose in MES buffer was loaded on the top of the gradient. Samples were centrifuged at 200,000×g for 16 hours at 4° C. 12×400 µl fractions were collected from top to bottom. 21 µl of each fraction was applied to 12% SDS-PAGE and then immunoblotted with anti-PrP, anti-flottlin-1 or anti-FLNa Mabs.

Immunoprecipitation, immunoblotting, and identification of co-purified proteins by Mass Spectrometry: to identify proteins that are normally bound to PrP in various tumor cell lines, cell lysates were prepared in Cell Signaling Co-I.P. Buffer (Cell Signaling Technology). Immunoprecipitation was performed with Mabs 8B4, 8H4, D7C7 or 1A10 that were conjugated to Sepharose beads (Pan, T. et al., *J Clin Microbiol.* 43(3): 1118-1126, 2005). Beads were collected by centrifugation and washed extensively (×6) with PBS-T. Bound proteins were eluted using IgG-Elution Buffer (Pierce). The eluted proteins were then separated by SDS-PAGE (12% gel) and silver stained (Bio-Rad). One of the unique bands at 280 kDa was cut out, washed, reduced/alkylated, and digested with trypsin. The digested products were then analyzed by mass spectrometry at the Case Center for Proteomics, Mass Spectrometry Core Facility using a LC-MS system (Finnigan LTQ linear ion trap mass spectrometer). Identification of the protein was based on peptide fragment sequence homology with FLNa in the NCBI database, using the search program, Mascot. All matching spectra were further verified by manual interpretation. The interpretation process was aided by additional searches using the programs Sequest and Blast. To confirm that the protein bound to PrP$^c$ was FLNa, immunoprecipitated proteins were separated by 12% SDS-PAGE, electro-transferred to nitrocellulose membrane, and blotted with an anti-FLNa Mab. Bound antibody was detected with a goat anti-mouse-HRP antibody using the chemiluminescence blotting system (Pierce).

Binding of GST-PrP23-253 to FLNa: 2 μg of Flag-FLNa dimer or Flag-FLNa1-23 were mixed with 3 μg of GST-PrP231-253 in 400 μl binding buffer (20 mM Tris.HCl, pH7.4, 150 mM NaCl, 1 mM EGTA and 0.1% Tween 20), respectively. GST was used as control. The tubes were rocked slowly and incubated at RT for 1 hr. 10 μl of GST binding beads (Novagen, pre-equilibrated with binding buffer) was added and further incubated for 30 min. The beads were then washed with binding buffer ×5 (5 min/time). The beads were resuspended in 15 μl of 2×SDS loading buffer and boiled at 95° C. for 10 min. The proteins were separated on 4-20% Tris-glycine gel and then transferred to NC membrane. FLNa was detected with anti-Flag Mab (Sigma, 1:1000 dilution, 4° C. overnight). After second antibody incubation and washing, the membrane was developed by the addition of SUPERSIG-NAL West Femito Maximum sensitive substrate (Pierce, 1:20 dilution).

Binding to pro-PrP: 250 ng of Flag-FLNa was mixed with 1.2 μg of rPrP23-253 or rPrP23-230 in 400 μl binding buffer (same as above). The tubes were rocked slowly and incubated at RT for 1 hr. Then 3 μg of anti-PrP Mab 8H4 was added and incubated for another hour with gentle rocking. 10 μl of protein G agarose beads (pre-equilibrated with binding buffer) was then added for 30 min. The beads were washed with binding buffer for 5 min.×5. The beads were then resuspended in 15 μl of 2×SDS loading buffer and boiled at 95° C. for 10 min. The proteins were separated on a 4-20% Tris-glycine gel and then transferred to NC membrane. FLNa was detected with anti-Flag Mab (Sigma, 1:1000 dilution, 4° C. overnight). After second antibody incubation and washing, the membrane was developed as described above. On the same membrane, input rPrPs were detected with anti-PrP Mab 8B4.

Competition of Co-I.P. with synthetic peptide: BxPC-3 and Panc.02.03 cell lysates were prepared as described in the co-i.p. experiment. Mab 8B4 conjugated beads were made as described by the provider (Pierce). Prior to the co-i.p. experiment, the efficiency of the beads was determined by direct immuno-precipitation of the cell lysate. For competition experiments, 400 μl of cell lysate from each cell type was loaded into the Mab 8B4 column. Synthetic peptides in the indicated amount were also added, as well as 4 μl of PMSF and 1 μl/column of DMSO. The columns were placed in the 4° C. cold room overnight with gentle rocking. Each column was then washed 6× with cell lysate buffer and eluted in 2×100 μl of Immunepure-IgG elution buffer (Pierce) in the cold room. Eluted proteins were separated in a 4-20% Tris-glycine gel, transferred to NC membrane and then immunoblotted with anti-FLNa Mab as described.

Cell surface biotinylation: PDAC tumor cells were surface incubated with sulfosuccinomidobiotin (Pierce) (0.1 mg/ml in labeling buffer (150 mM NaCl, 0.1 M Hepes, pH.8)) for 30 min as described by Liu, D. et al., *J Exp Med.* 183:1987-1994 (1996). After biotinylation cells were washed, lysed and immunoprecipitated with avdin conjugated beads in the co-immunoprecipitation buffer. Bound proteins were then eluted and immunoblotted with anti-PrP, anti-FLNa or anti-HSP90 Mabs. The flow-through from the avidin-bead column, which contains the non-biotinylated cytosolic protein was also collected and then immunoblotted with the same Mabs.

Co-localization of PrP and FLNa in different tumor cells: seeded tumor cells were first assayed for filamin A expression as described earlier. The cells were then blocked with normal mouse serum (1 mg/ml) for 1 hour at 20° C. PrP was then detected with biotinylated 8H4 (0.01 μg/μl) or biotinylated anti-CD55 (BD Biosciences) as control. Streptavidin Alexa Fluor 555 (Invitrogen) was applied to detect bound biotinylated antibodies. Nuclei were detected with DAPI.

Sandwich ELISA for quantifying the level of soluble PrP in the culture supernatant of the PDAC cell lines: $1 \times 10^5$ of each PDAC cell line in 200 ml of culture medium was cultured in 96 well tissue culture plate (Corning, N.Y.) in triplicate. Twenty fours after culture, 100 ml of the culture medium was carefully removed. The level of soluble PrP present in the culture medium was then assayed using a sandwich EILSA as described by us. In this sandwich ELISA, Mab 8B4 was used as a capture-antibody and a biotinylated Mab 7A12 as used as a detecting antibody. The results presented represent the average of the triplicate well +/−S.E.

Immunohistochemical staining: unstained, 5m sections were cut from paraffin blocks of selected cases and de-paraffinized using standard techniques. Slides were treated with 1× sodium citrate buffer (diluted from 10× heat-induced epitope retrieval buffer; Ventana-Bio Tek Solutions, Tucson, Ariz.) before heating for 20 min. in a microwave oven. Slides were then cooled at room temperature for 20 min., and incubated with 3% w/v $H_2O_2$ for 10 min. Mouse anti-human PrP Mab, 8H4, was then added and incubated at room temperature for 1 hr. An isotype control Mab D7C7 was included in all experiments as a negative control. After serial washing, bound primary antibody was detected by adding a secondary antibody followed by avidin-biotin complex and 3,3'-diaminobenzidine (DAB) (Dako Inc, CA). Sections were counterstained with hematoxylin. Each slide was coded and evaluated by two pathologists (W. X and A. A. P.). The cytoplasmic and membrane staining intensity of each sample was graded as diffuse (>50% neoplastic cells stained positive), focal positive (5-50% neoplastic cells stained positive) or negative (<5% neoplastic cells stained). The identity of the case was revealed only after a score had been given. The process to detect GPI-SS of pro-prion protein in tumor sample was described above. Instead of 8H4, rabbit polyclonal antibody specific for the PrP GPI-PSS or non-immune serum was added and the second step antibody was a goat anti-rabbit Ig antibody.

Statistical analysis: the frequencies of PrP immunostaining among normal pancreas, pancreatic precursor lesions and cancer samples were analyzed by the $\chi^2$ test or Fisher's exact test to account for frequency values<5. For purposes of statistical analysis, all positive staining carcinomas were combined for comparison to negative staining cancers. The Kaplan-Meier method was used to determine overall survival with respect to $PrP^c$ expression. All 37 patients analyzed had surgery done in years from 2001 to 2003. None of these patients had pre-surgical chemotherapy or radiation therapy.

Results

PrP exists as pro-PrP in PDAC cell lines: human PrP is synthesized as a 253 amino acid long pre-pro-PrP (FIG. 3A). The N-terminus has a leader signal sequence. The C-terminal end has the GPI-PSS. These sequences are removed in the endoplasmic reticulum (ER) and thus are absent from mature PrP. The protein backbone of mature PrP has a Mol. Mass of about 23 kDa. Addition of two N-linked glycans and a GPI anchor completes the maturation of GPI-anchored PrP.

When stained with a well-characterized anti-PrP Mab, 8H4 (Zanusso, G. et al., (1998) *Proc Natl Acad Sci.* USA 95, 8812-8816; Li, R. et al., (2000) *J Mol. Biol.* 301, 567-573), we found that PrP is expressed in a panel of seven human PDAC cell lines: BxPC 3, Panc 02.03, PL45, Capan 1, CFPAC 1, Panc 1 and Panc 10.05 as well as in a human neuroblastoma cell line, WV (FIG. 3B). While most of the PrP detected in WV cells is on the cell surface, in the human PDAC cell lines, PrP is detected on the cell surface as well as in the cytoplasm (FIG. 3B). The level of PrP varies among PDAC cell lines; BxPC 3 cells appear to have highest level of PrP on the cell surface. This interpretation was confirmed by staining of live PDAC cell lines with Mab 8H4 and flow cytometry analysis (FIG. 3C).

Figure 4:
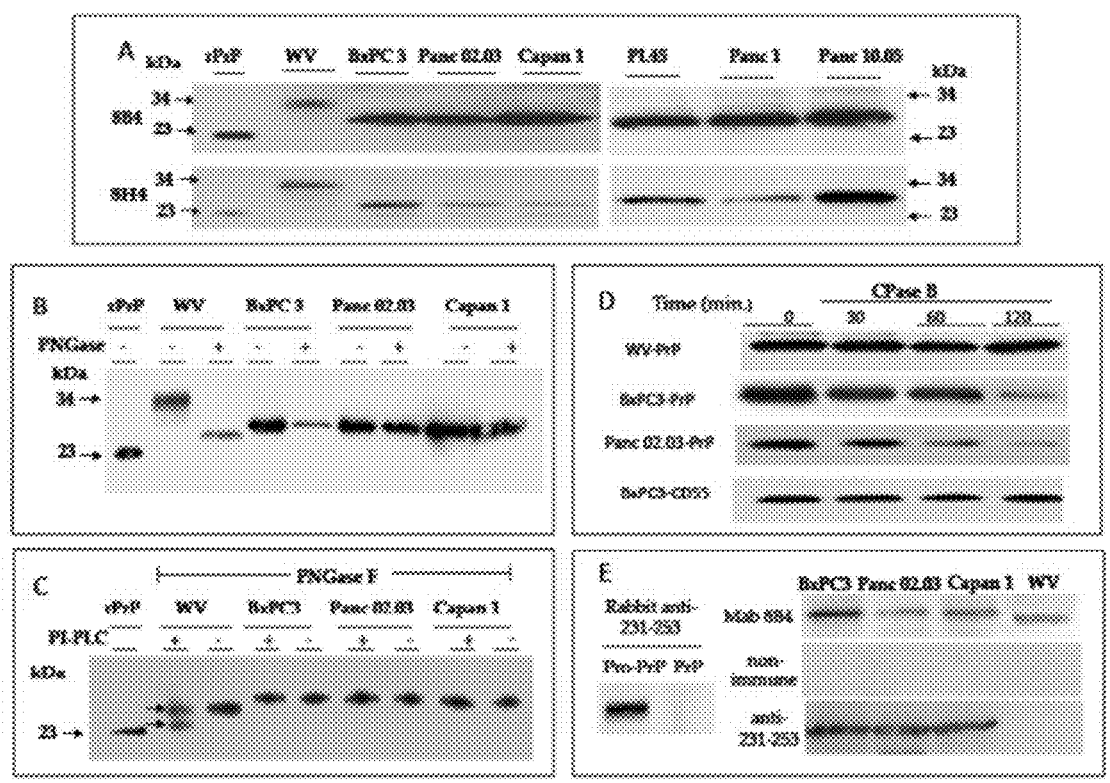
FIGS. 4A-E are a series of immunoblots showing that PrP in the PDAC cell lines exists as pro-PrP.

When immunoblotted with an N-terminus specific anti-PrP Mab, 8B4, or a C-terminus specific anti-PrP Mab, 8H4 (Zanusso, G. et al., (1998) *Proc Natl Acad Sci. USA* 95, 8812-8816; Li, R. et al., (2000) *J Mol Biol.* 301, 567-573), PrP from WV cells migrated as a 33-34 kDa protein due to the addition of the two N-linked glycans (FIG. 4A). In contrast, PrP from the PDAC cell lines migrated with an apparent Mol. Mass of 26 kDa (FIG. 4A). Because PrP from the PDAC cell lines has similar Mol. Mass, in subsequent studies, we concentrated our studies on three of the PDAC cell lines, BxPC 3, Panc 02.03 and Capan 1.

To determine whether PrP in the three PDAC cell lines contains N-linked glycans, we treated the cell lysates with endoglycosidase-F (PNGase-F) prior to immunoblotting. Deglycosylation reduced the Mol. Mass of PrP from WV cells from 34 kDa to 25.5 kDa (FIG. 4B). Identical treatment did not change the mobility of PrP from the PDAC cell lines. Hence, in the PDAC cell lines PrP is unglycosylated.

Figure 8:
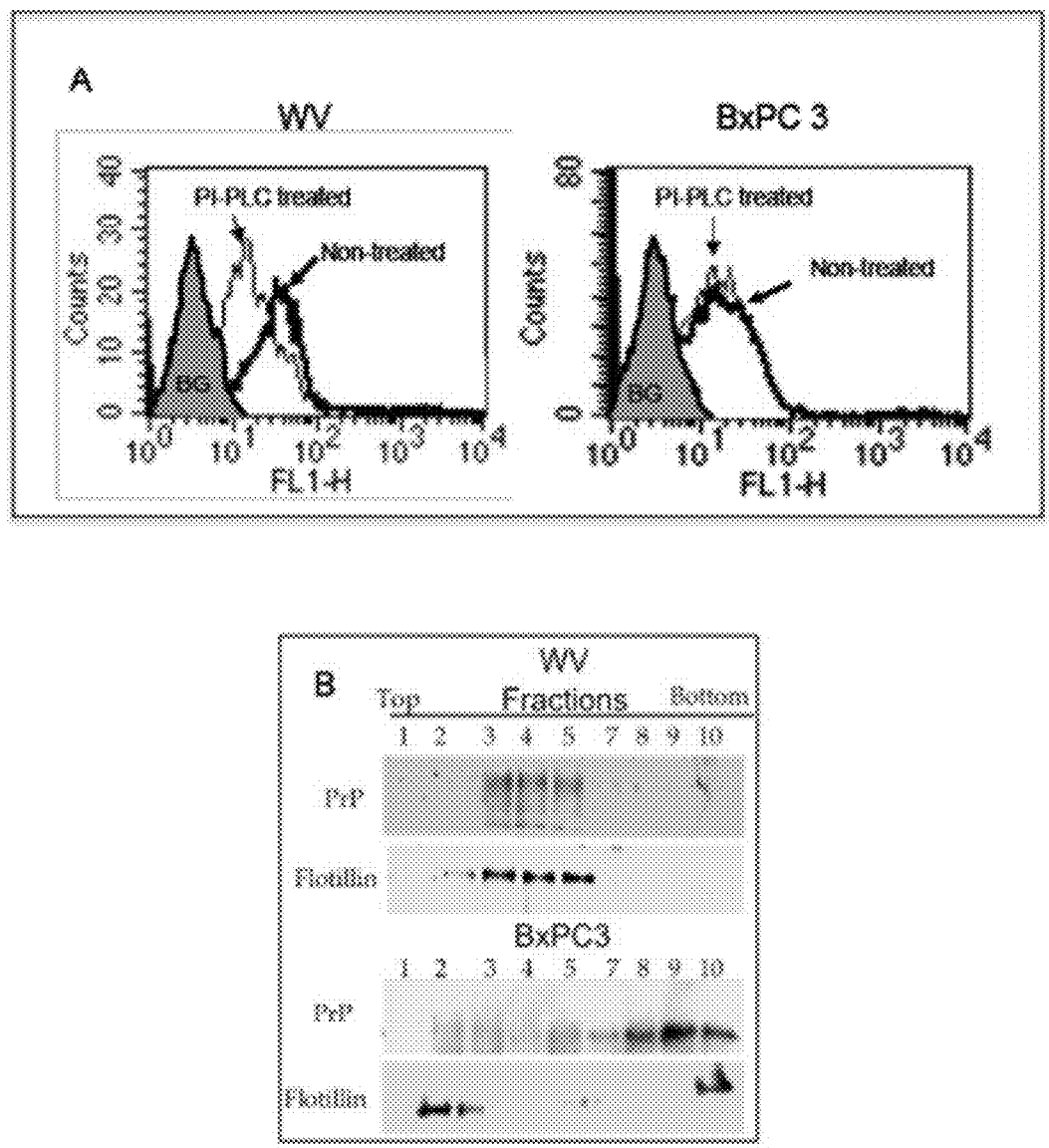
FIGS. 8A-B illustrate cell surface PrP on PDAC cells.

Deglycosylated PrP from WV cells migrated slightly faster than PrP from the PDAC cell lines (FIG. 4B). We therefore determined whether PrP is GPI-anchored in the PDAC cell lines. Affinity-purified, deglycosylated PrP was treated with phospholipase C (PI-PLC) to remove the GPI anchor prior to immunoblotting. After treatment, PrP from WV cells separated into two species, 25.5 and 25 kDa (FIG. 4C). In the 25 kDa PrP the GPI anchor has been removed. This species represents 40-60% of the total PrP in WV cells (n=3). The 25.5 kDa species is the deglycosylated PrP that is not cleaved by PI-PLC. Some GPI anchors are resistant to PI-PLC due to the acylation of an inositol hydroxyl group in the anchor (Maeda, Y. et al., *Methods Enzymol.* 416, 182-205). Identical treatment did not change the mobility of PrP from the PDAC cells. Thus, PrP in these PDAC cell lines is either not GPI-anchored or its GPI anchor is resistant to PI-PLC. This conclusion is consistent with our finding that treatment of live BxPC 3 and Panc 02.03 cells with PI-PLC did not reduce the level of cell surface PrP, as revealed by flow-cytometry analysis (FIG. 8A).

Carboxypeptidase (CPase) removes amino acids from the C-termini of proteins (Ambler, R. P. (1967) *Meth. in Enzymol.* 11, 155-166). GPI-anchored proteins should be resistant to CPase because their C-termini are protected by the lipid anchors. If PrP from the PDAC cell lines lacks a GPI anchor, it should be susceptible to CPase. To test this hypothesis, affinity purified, deglycosylated PrP from each cell line was treated for different periods of time with CPase B ((Ambler, R. P. (1967) *Meth. in Enzymol.* 11, 155-166) prior to immunoblotting. As expected, PrP from WV cells is resistant to CPase B (FIG. 4D). However, after incubating with CPase B for 2 hrs, the levels of PrP from BxPC-3 and Panc.02.03 cells were reduced by 80% (n=3). By contrast, CD55, another GPI-anchored protein in BxPC-3 cells, is resistant to CPase B.

Figure 9:
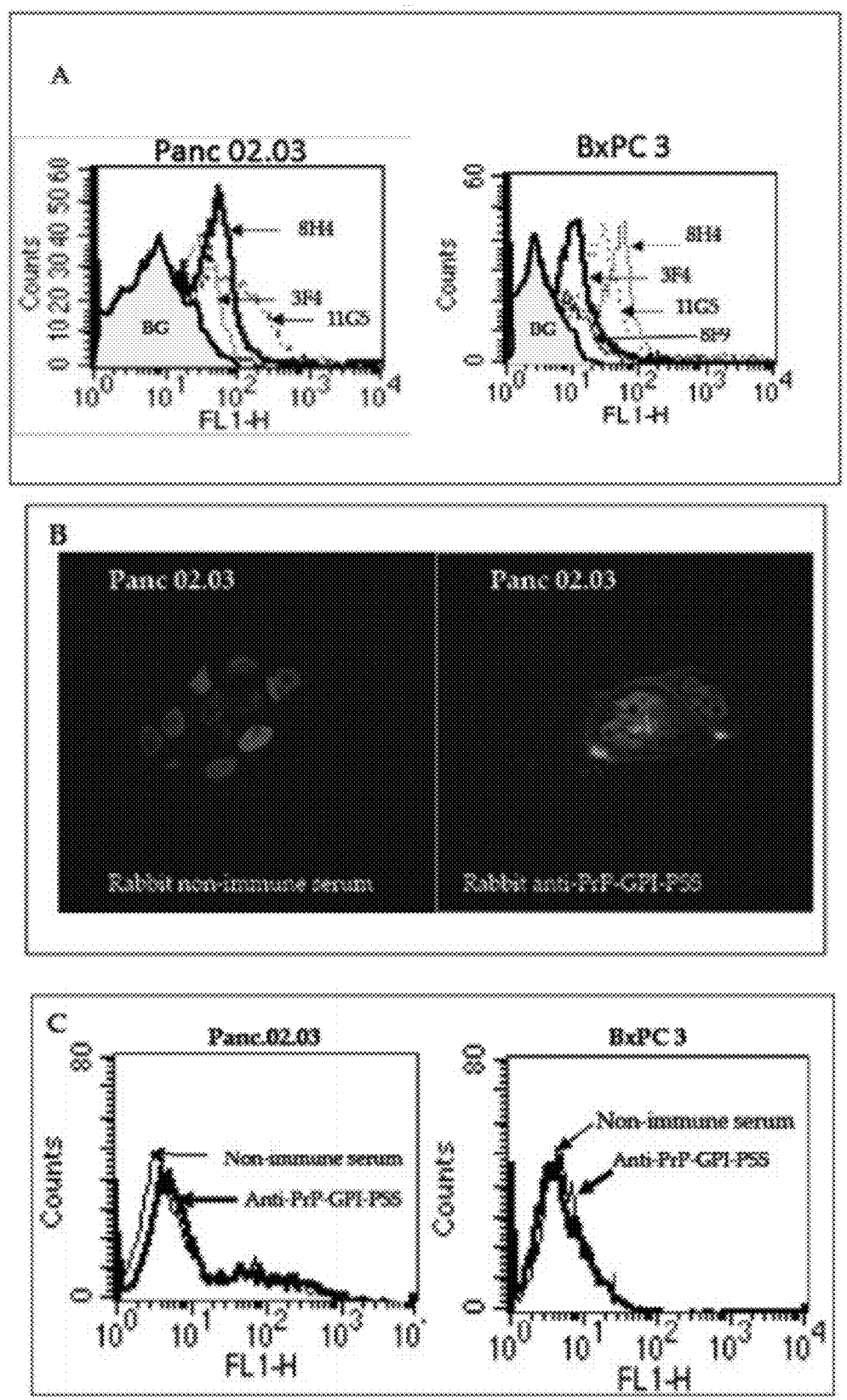
FIGS. 9A-C illustrate the topology of pro-PrP on the cell surface.

GPI-anchored proteins are present in lipid rafts (Ikezawa, H. (2002) *Biol Pharm Bull.* 25, 409-417; Rajendran, L. et al., (2005) *J Cell Sci.* 118, 1099-1102). Because PrP in the PDAC cell lines lacks a GPI anchor, PrP is no longer detected in lipid rafts in BxPC 3 cells, while flotillin-1, a lipid raft residential protein, still remains in lipid rafts (FIG. 9B).

Based on the SDS-PAGE mobility of PrP from the PDAC cell lines, we speculate that PrP in the PDAC cells may still have its GPI-PSS. To test this hypothesis, we generated a polyclonal antiserum in rabbits that is specific for the GPI-PSS of PrP. The antiserum reacts with a recombinant pro-PrP23-253, which contains the GPI-PSS, but not with a mature PrP23-231, which lacks the GPI-PSS (FIG. 4E). The anti-GPI-PSS antiserum also reacts with affinity-purified PrP from all the three PDAC cell lines but not with affinity-purified PrP from WV cells (FIG. 4E). Pro-PrP is a precursor of mature PrP. The fact that no pro-PrP in WV cells is detected suggests that either the processing of PrP or the removal of the unprocessed pro-PrP is more rapid in WV cells. Collectively, these results provide conclusive evidence that in the PDAC cell lines PrP exists as pro-PrP.

Despite lacking a GPI anchor, some PrP is detected on the surface of PDAC cell lines (FIG. 3C). We speculate that some cell surface PrP may represent pro-PrP with its GPI-PSS inserted into the membrane and that the GPI-PSS is functioning as a surrogate trans-membrane anchor domain, a scenario that has been suggested by others (Rajendran, L. et al., (2005) J Cell Sci. 118, 1099-1102). This hypothesis is consistent with our findings that four different anti-PrP Mabs, which react with epitopes spread along the PrP, react with cell surface PrP (FIG. 9A). Furthermore, while the anti-PrP-GPI-PSS antiserum reacts with fixed PDAC cells (FIG. 9B), it does not react with live PDAC cells (FIG. 9C). Therefore, on the cell surface, the ectodomain of PrP is available to antibody binding but the GPI-PSS is not.

Figure 5:
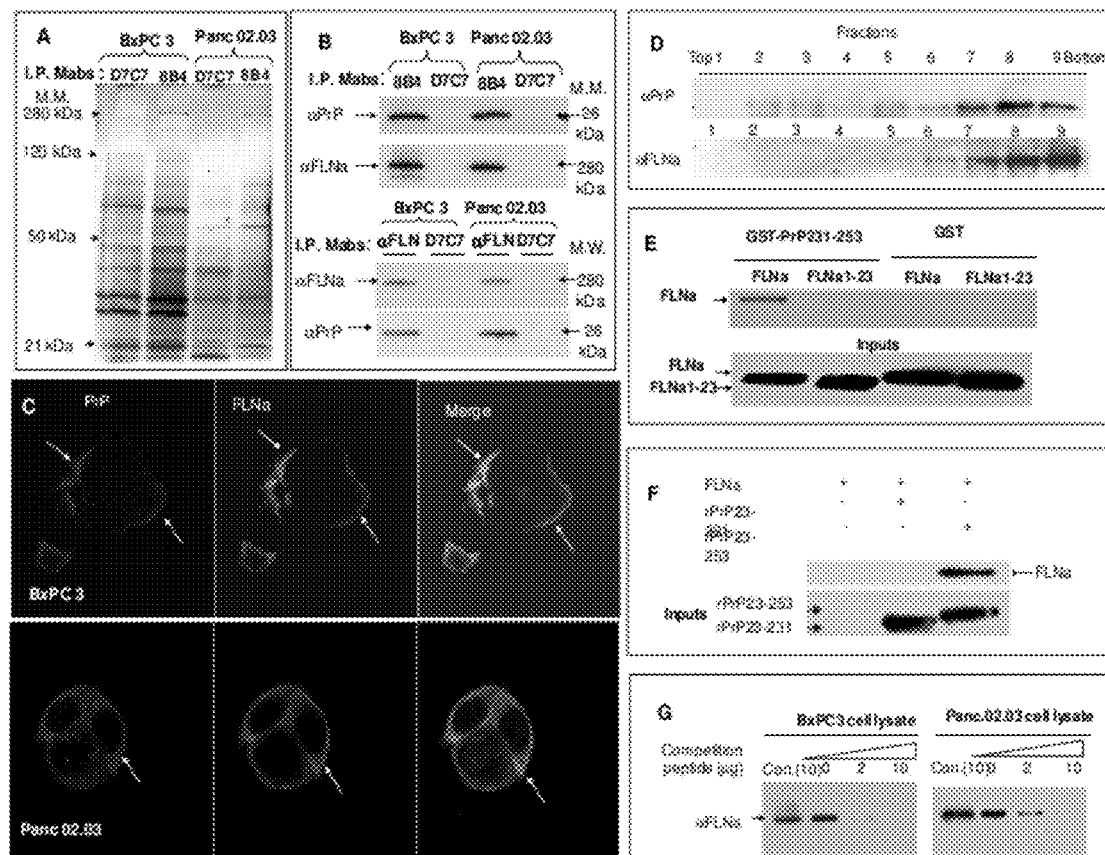
FIGS. 5A-G show filamin A (FLNa) binding to the GPI-PSS of pro-PrP.

The PrP GPI-PSS binds to filamin A: we next sought to identify cellular proteins that interact with PrP in the PDAC cell lines. Co-immunoprecipitation with Mab 8B4, but not an irrelevant Mab, D7C7, identified a prominent band with a Mol. Mass of 280 kDa in BxPC 3 and Panc 02.03 cell lysates (FIG. 5A). The protein was sequenced by mass-spectrometry and found to be filamin A (FLNa), an actin associated protein that integrates cell mechanics and signaling (Stossel, T. P. et al (2001) Nat Rev Mol Cell Biol. 2, 138-145; Feng, Y. et al., (2004) Nat Cell Biol. 6, 1034-1038).

The identity of FLNa was confirmed by immunoblotting of proteins co-purified with PrP with an FLNa specific Mab (FIG. 5B). Conversely, immunoblotting of proteins co-purified with FLNa with an anti-PrP Mab also revealed the presence of PrP (FIG. 5B). Furthermore, PrP and FLNa also partially co-localize in BxPC 3 and Panc 02.03 cells (FIG. 5C), and are present in similar fractions in a sucrose gradient (FIG. 5D). In WV cells, PrP did not co-purify with FLNa because WV cells do not express FLNa (n.s.).

Native FLNa is a homodimer; each subunit contains a spectrin-related F-actinbinding domain followed by 24 Ig-like domains (Stossel, T. P. et al., (2001) Nat Rev Mol Cell Biol. 2, 138-145; Feng, Y. et al., (2004) Nat Cell Biol. 6, 1034-1038). The CD faces of FLNa Ig-like domains are common binding sites for all FLNa-partners for which atomic structures have been resolved. In addition, these FLNa binding partners share a conserved hydrophobic amino acid motif (Nakamura, F. et al., (2006) Blood 107, 1925-1932) (FIG.

4E). Interestingly, ClustalW alignment suggests that the GPI-PSS of pro-PrP contains the FLNa binding motif (FIG. 5E). We thus investigated whether FLNa indeed binds the GPI-PSS of PrP.

In an in vitro pull down experiment, we found that full-length FLNa dimer but not FLNa1-23 monomer, which lacks the last Ig-like dimerization domain (Nakamura, F. et al., (2007) J Cell Biol. 179, 1011-1025), bound PrP GPI-PSS GST fusion protein (FIG. 5E). The full-length FLNa also bound pro-PrP23-253 but not mature PrP23-231 (FIG. 5F). These findings were further confirmed in BxPC-3 and Panc.02.03 cells. The levels of FLNa co-purified with pro-PrP in these cell lines could be competed with a PrP GPI-PSS synthetic peptide, but not with a control peptide (FIG. 5G). Similar results were obtained with Capan 1 cells (n.s.).

PrP, but not FLNa, is readily detected in the membrane fraction when PDAC cell lysate was fractionated with a membrane protein extraction reagent kit (n.s.). Thus, PrP, but not FLNa, is embedded in the membrane. The high concentration of salts and detergent in the extraction buffer has probably prevented the co-fractionation of FLNa and PrP. We next determined whether FLNa, which is present near the inner membrane leaflet (Stossel, T. P. et al., (2001) Nat Rev Mol Cell Biol. 2, 138-145), interacts with membrane PrP. We labeled the cell surface of PDAC cell lines with biotin and then immunoprecipitated the biotinylated proteins with avidin-conjugated beads, using the co-immunoprecipitation buffer. Bound proteins were then eluted and immunoblotted with Mabs specific for PrP, FLNa or Hsp 90. Hsp 90 is a cytosolic protein and is used as a control to determine whether contaminating cytosolic proteins are present in the cell surface protein preparation. It is clear that proteins bound to avidin beads contain PrP and FLNa, but not Hsp90. On the other hand, all three proteins are present in the flow through fraction, which includes cytosolic proteins. In another series of experiments, we showed that PrP, but not FLNa, is readily biotinylated 9 on the cell surface (n.s.). Collectively, these results suggest that FLNa interacts with cell surface PrP.

Pro-PrP is detected in a subgroup of resectable human PDAC cases and expression is associated with poorer prognosis: to determine whether our findings in cell models have clinical relevance, we carried out a retrospective study on the expression of PrP in human PDAC biopsies by immunohistochemistry. Tissues from patients with chronic pancreatitis or PanIN lesions served as controls. In normal human pancreas (FIG. 6A-D), only islet cells (B) showed moderate PrP staining; neither acinar (C) nor ductal epithelial cells (D) stained for PrP. PrP was also undetectable in the duct cells in chronic pancreatitis (n=20), PanIN-1 (n=28) and PanIN-2 (n=40) (n.s.). Four of 30 (13.3%) PanIN-3 specimens showed weak staining for PrP (n.s.). Among the 83 resectable PDAC cases, 34 (41%) showed strong staining for PrP (FIG. 6E-H) (Summarized in Table 1).

TABLE 1

Summary of Staining Results

|  | Total Cases | $PrP^{C+}$ cases |
|---|---|---|
| Controls[a] | 20 | 0 |
| PanIN-1 | 28 | 0 |
| PanIN-2 | 40 | 0 |
| PanIN-3 | 30 | 4 (13%) |
| PDAC[b] | 83 | 34 (41%) |

[a]The 20 cases (11 males and 9 females) of controls had a mean patient age of 61.3 years.
[b]The mean patient age was 63.2 years and included 49 males and 34 females.

Figure 6:
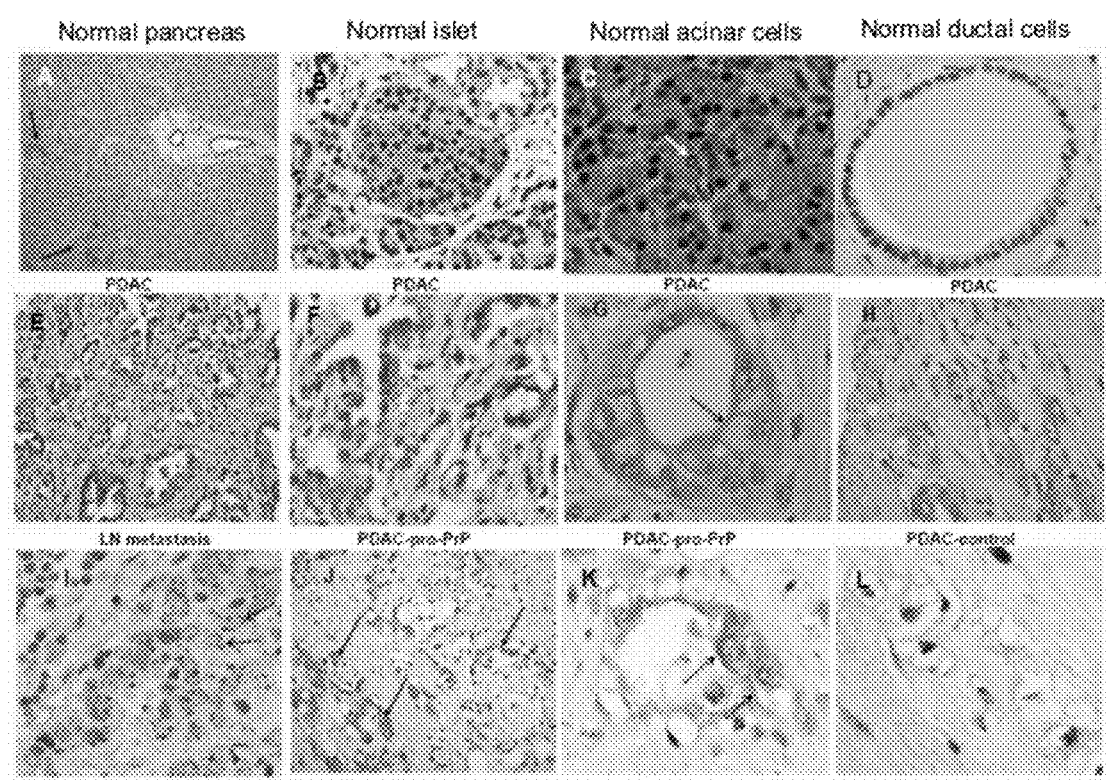
FIGS. 6A-L are a series of immunohistochemical stains showing that PrP is present in PDAC lesions but not in normal ductal cells. Immunohistochemical staining shows that in normal pancreas, only islet cells (arrows) express PrP (FIGS. 6A-B); neither acinar cells (FIG. 6C, arrow shows a centroaciner cell) nor ductal cells (FIG. 6D) express PrP. In PDAC, malignant ductal cells express high levels of PrP (FIGS. 6E-H are from different cases, dash arrow in FIG. 5G suggests immunoreactivity on the cell surface). PDAC lymph node metastases also express high levels of PrP (FIG. 6J). PrP in PDAC lesions exits as pro-PrP because the tumor cells react strongly with anti-PrP-GPI-PSS antiserum (FIGS. 6J-K) (dash arrows in FIG. 6K suggest cell surface immunoreactivity). The control antiserum only has background immunoreactivity (FIG. 6L)

PrP immunoreactivity was also detected in the corresponding lymph node metastases (FIG. 6I). All PDAC tumor cells reacted strongly with the anti-GPI-PSS antiserum (FIGS. 6J-K). However, stromal cells surrounding the tumor cells were negative. Staining with the control antiserum was negative (FIG. 6L). Thus, as in the PDAC cell lines, PrP exists as pro-PrP in human PDAC lesions.

Figure 7:
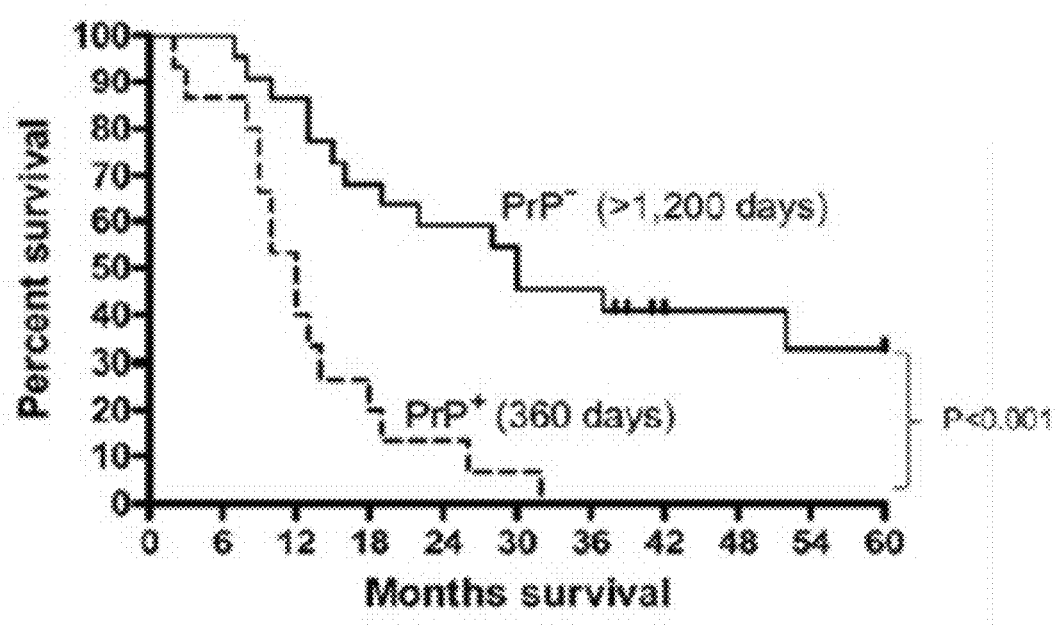
FIG. 7 is a Kaplan-Meier survival curve illustrating that expression of PrP is associated with poorer prognosis. The 37 patients had surgery done from 2001 to 2003. Patients (n=16) whose tumor expressed PrP had a medium survival time of 360 days. On the other hand, of the 21 patients, whose tumor lacked PrP, six of these patients are still alive as of October of 2008. Four of these patients have already passed 5 years after surgery; two others will have passed 5-year in late November of 2008 (two of the spikes). The other two spikes, one died 41 months and the other died 52 months after surgery. This cohort of patient has mean survival time of >1,200 days (P<0.001)

We next investigated whether PrP expression correlates with the clinical outcome in the group of 37 patients who had surgery done between 2001 and 2003. We observed that the expression of PrP is associated with shorter survival (FIG. 7). Patients (n=16) whose tumor showed strong PrP immunoreactivity had a shorter median survival time of 360 days, whereas patients (n=21) whose tumor did not show PrP immunoreactivity had a median survival time of >1,200 days (P<0.001). Furthermore, we did not find any other factors, such as age, gender, tumor size or differentiation that are clearly associated with prognosis.

From the above description of the invention, those skilled in the art will perceive improvements, changes and modifications. Such improvements, changes, and modifications are within the skill of the art and are intended to be covered by the appended claims. All publications, patents, and patent applications cited in the present application are herein incorporated by reference in their entirety.

Having described the invention, the following is claimed:

1. A method of detecting cancer in a subject, the method comprising the steps of:
   obtaining a bodily sample from the subject;
   detecting the level of pro-prion protein (pro-PrP), not mature PrP, in the bodily sample; and
   comparing the level of pro-PrP in the bodily sample to a control level;
   wherein an increased level of pro-PrP in the bodily sample as compared to the control level indicates that the subject has cancer.

2. The method of claim 1, the bodily sample comprising a peripheral bodily fluid selected from the group consisting of blood, plasma, urine, mucus, bile, juice, supernatant fluid, and serum.

3. The method of claim 1, the bodily sample comprising a tissue biopsy.

4. The method of claim 1, the cancer being pancreatic cancer and the bodily sample comprising a pancreatic secretion selected from the group consisting of pancreatic juice and bile.

5. The method of claim 1, wherein the step of detecting the level of pro-PrP in a bodily sample includes:
   contacting the bodily sample with a capture moiety that binds to pro-PrP but not mature PrP, the capture moiety comprising filamin A (FLNa) or an antibody or antibody fragment thereof that binds to a GPI anchor peptide signal sequence (GP-PSS) of pro-PrP; and
   detecting the level of pro-PrP that binds to the capture moiety.

6. The method of claim 5, the GPI-PSS having the amino acid sequence of SEQ ID NO: 1.

7. The method of claim 5, the capture moiety comprising an antibody or fragment thereof that binds to SEQ ID NO: 1.

8. The method of claim 5, the capture moiety comprising filamin A (FLNa).

9. A method of detecting pancreatic cancer in a subject, the method comprising the steps of:
   obtaining a bodily sample from the subject;
   detecting the level of pro-PrP, not mature Prp, in the bodily sample; and
   comparing the level of pro-PrP in the bodily sample to a control level;
   wherein an increased level of pro-PrP in the bodily sample as compared to the control level indicates that the subject has pancreatic cancer.

10. The method of claim 9, the pancreatic cancer being ductal adenocarcinoma.

11. The method of claim 9, the bodily sample comprising a pancreatic secretion selected from the group consisting of pancreatic juice and bile.

12. The method of claim 9, wherein the step of detecting the level of pro-PrP in a bodily sample includes:
    contacting the bodily sample with a capture moiety that binds to pro-PrP but not mature PrP, the capture moiety comprising FLNa or an antibody or antibody fragment thereof that binds to a GPI anchor peptide signal sequence (GP-PSS) of pro-PrP; and
    detecting the level of pro-PrP that binds to the capture moiety.

13. The method of claim 12, the GPI-PSS having the amino acid sequence of SEQ ID NO: 1.

14. The method of claim 12, the capture moiety comprising an antibody or fragment thereof that binds to SEQ ID NO: 1.

15. The method of claim 12, the capture moiety comprising FLNa.

16. A method for evaluating the prognosis of a subject having pancreatic cancer, the method comprising the steps of:
    obtaining a bodily sample from the subject, the bodily sample comprising a pancreatic secretion selected from the group consisting of pancreatic juice and bile;
    detecting the level of pro-PrP, not mature Prp, in the bodily sample; and
    comparing the level of pro-PrP in the bodily sample to the control level;
    wherein the presence of pro-PrP in the bodily sample is indicative of a poor prognosis, the poor prognosis including a median survival time of less than about 1 year.

17. The method of claim 16, the pancreatic cancer being ductal adenocarcinoma.

18. The method of claim 16, wherein the step of detecting the level of pro-PrP in a bodily sample includes:
    contacting the bodily sample with a capture moiety that binds to pro-PrP but not mature PrP, the capture moiety comprising FLNa, or an antibody or antibody fragment thereof that binds to a GPI anchor peptide signal sequence (GP-PSS) of pro-PrP; and
    detecting the level of pro-PrP that binds to the capture moiety.

19. The method of claim 18, the GPI-PSS having the amino acid sequence of SEQ ID NO: 1.

20. The method of claim 18, the capture moiety comprising an antibody or fragment thereof that binds to SEQ ID NO: 1.

21. The method of claim 18, the capture moiety comprising FLNa.

* * * * *

SEQUENCE LISTING

```
<160> NUMBER OF SEQ ID NOS: 1

<210> SEQ ID NO 1
<211> LENGTH: 23
<212> TYPE: PRT
<213> ORGANISM: Artificial Sequence
<220> FEATURE:
<223> OTHER INFORMATION: Synthetic peptide corresponding to
      the GPI-PSS of pro-PrP

<400> SEQUENCE: 1

Gly Ser Ser Met Val Leu Phe Ser Ser Pro Pro Val Ile Leu Leu Ile
1               5                   10                  15

Ser Phe Ile Phe Leu Val Gly
            20
```